United States Patent
Park et al.

(10) Patent No.: US 10,290,818 B2
(45) Date of Patent: May 14, 2019

(54) ORGANOMETALLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Sangho Park, Anyang-si (KR); Wook Kim, Suwon-si (KR); Changho Noh, Suwon-si (KR); Hyejin Bae, Suwon-si (KR); Virendra Kumar Rai, Hwaseong-si (KR); Satoko Ishibe, Seongnam-si (KR); Miyoung Chae, Suwon-si (KR); Dmitry Kravchuk, Hwaseong-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 282 days.

(21) Appl. No.: 15/064,112

(22) Filed: Mar. 8, 2016

(65) Prior Publication Data
US 2017/0110673 A1    Apr. 20, 2017

(30) Foreign Application Priority Data
Oct. 14, 2015    (KR) .................. 10-2015-0143371

(51) Int. Cl.
*H01L 51/00* (2006.01)
*C07F 15/00* (2006.01)
(Continued)

(52) U.S. Cl.
CPC ...... *H01L 51/0085* (2013.01); *C07F 15/0033* (2013.01); *C09K 11/06* (2013.01); *C09K 2211/185* (2013.01); *H01L 51/5016* (2013.01)

(58) Field of Classification Search
CPC ............. H01L 51/0085; H01L 51/5016; C07F 15/0033; C09K 11/06; C09K 2211/185
(Continued)

(56) References Cited

U.S. PATENT DOCUMENTS 7,585,573 B2 *  9/2009  Lee ..................... C07F 15/0033
                                                    252/301.16
9,978,961 B2 *  5/2018  Tsai .................... H01L 51/0085
(Continued)

FOREIGN PATENT DOCUMENTS

JP    2011-256116 A    12/2011
JP    2012-019171 A    1/2012
(Continued)

*Primary Examiner* — Michael Bernshteyn
(74) *Attorney, Agent, or Firm* — Cantor Colburn LLP

(57) ABSTRACT

An organometallic compound represented by Formula 1:

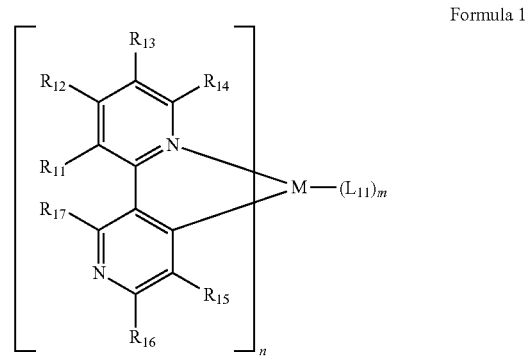

Formula 1 wherein, in Formula 1, $L_{11}$, M, $R_{11}$ to $R_{17}$, m, and n are the same as described in the specification.

19 Claims, 3 Drawing Sheets

(51) Int. Cl.
*C09K 11/06* (2006.01)
*H01L 51/50* (2006.01)

(58) Field of Classification Search
USPC .......................................................... 428/690
See application file for complete search history.

(56) References Cited

U.S. PATENT DOCUMENTS

2013/0292654 A1\* 11/2013 Matsunaga ............ C09K 11/06
257/40
2013/0313532 A1\* 11/2013 Watanabe ........... H01L 51/0071
257/40

FOREIGN PATENT DOCUMENTS

| | | |
|---|---|---|
| JP | 2013-243299 A | 12/2013 |
| KR | 2005-0078472 A | 8/2005 |
| KR | 2015-0083017 A | 7/2015 |

\* cited by examiner

ORGANOMETALLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0143371, filed on Oct. 14, 2015, in the Korean Intellectual Property Office, the content of which is incorporated herein in its entirety by reference.

BACKGROUND

1. Field

The present disclosure relate to an organometallic compound and an organic light-emitting device including the same.

2. Description of the Related Art

Organic light-emitting devices (OLEDs) are self-emission devices that have wide viewing angles, high contrast ratios, and short response times. In addition, the OLEDs display excellent brightness, driving voltage, and response speed characteristics, and produce full-color images.

A typical organic light-emitting device includes an anode, a cathode, and an emission layer disposed between the anode and the cathode. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

Provided are organometallic compounds and organic light-emitting devices including the same.

Additional aspects will be set forth in part in the description which follows and, in part, will be apparent from the description, or may be learned by practice of the presented exemplary embodiments.

According to an aspect of an exemplary embodiment, provided is an organometallic compound represented by Formula 1:

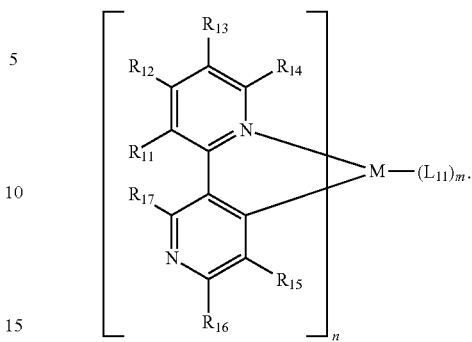

Formula 1

In Formula 1,

M is selected from a Period 4 transition metal, a Period 5 transition metal, and a Period 6 transition metal, europium (Eu), terbium (Tb), and thulium (Tm);

$R_{11}$ to $R_{17}$ are each independently selected from hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); two adjacent groups selected from $R_{11}$ to $R_{17}$ are optionally linked to each other to form a saturated or unsaturated ring;

at least one of $R_{15}$ and $R_{17}$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$Q_1$ to $Q_3$ are each independently selected from a substituted or unsubstituted $C_1$-$C_{60}$ alkyl group, a substituted or unsubstituted $C_3$-$C_{10}$ cycloalkyl group, a substituted or unsubstituted $C_6$-$C_{60}$ aryl group, and a substituted or unsubstituted $C_1$-$C_{60}$ heteroaryl group;

n is selected from 1, 2, and 3;

$L_{11}$ is selected from a monodentate ligand and a bidentate ligand;

m is selected from 0, 1, 2, 3, and 4.

According to an aspect of another exemplary embodiment, an organic light-emitting device includes:

a first electrode;

a second electrode; and an organic layer between the first electrode and the second electrode, wherein the organic layer including an emission layer, and wherein the organic layer comprises at least one organometallic compound represented by Formula 1.

The emission layer may include the organometallic compound, the emission layer may further include a host, and the organometallic compound included in the emission layer may act as a dopant.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
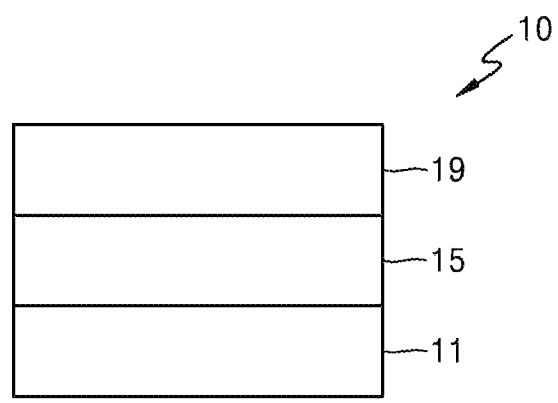
FIG. 1 is a schematic cross-sectional view of an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present inventive concept. As used herein, the term "and/or" includes any and all combinations of one or more of the associated listed items. Expressions such as "at least one of," when preceding a list of elements, modify the entire list of elements and do not modify the individual elements of the list It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context dearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

An organometallic compound according to an embodiment is represented by Formula 1:

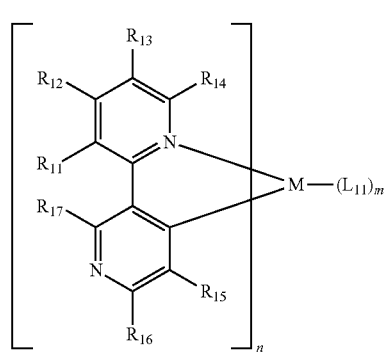

Formula 1

M in Formula 1 may be selected from a Period 4 transition metal, a Period 5 transition metal, and a Period 6 transition metal, europium (Eu), terbium (Tb), and thulium (Tm).

For example, M in Formula 1 may be selected from iridium (Ir), platinum (Pt), osmium (Os), ruthenium (Ru), rhodium (Rh), palladium (Pd), copper (Cu), silver (Ag), gold (Au), titanium (Ti), zirconium (Zr), hafnium (Hf), europium (Eu), terbium (Tb), and thulium (Tm), but is not limited thereto.

In various embodiments, M in Formula 1 may be selected from Ir, Pt, Os, Ti, Zr, Hf, Eu, Tb, and Tm, but is not limited thereto.

In various embodiments, M in Formula 1 may be selected from Ir, Pt, and Os, but is not limited thereto.

In various embodiments, M in Formula 1 may be selected from Ir and Pt, but is not limited thereto.

In various embodiments, M in Formula 1 may be Ir, but is not limited thereto.

$R_{11}$ to $R_{17}$ in Formula 1 may each independently be selected from hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

two adjacent groups selected from $R_{11}$ to $R_{17}$ may be optionally linked to each other to form a saturated or unsaturated ring;

at least one of $R_{15}$ and $R_{17}$ may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and $Q_1$ to $Q_3$ may each independently be selected from a substituted or unsubstituted $C_1$-$C_{60}$ alkyl group, a substituted or unsubstituted $C_3$-$C_{10}$ cycloalkyl group, a substituted or unsubstituted $C_6$-$C_{60}$ aryl group, and a substituted or unsubstituted $C_1$-$C_{60}$ heteroaryl group.

For example, $R_{17}$ in Formula 1 may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, but is not limited thereto.

For example, $R_{11}$ to $R_{17}$ in Formula 1 may each independently be selected from hydrogen, deuterium, —F, —Cl, —Br, —I, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); two adjacent groups selected from $R_{11}$ to $R_{17}$ may be optionally linked to each other to form a saturated or unsaturated ring;

at least one of $R_{15}$ and $R_{17}$ may be selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group; and $Q_1$ to $Q_3$ may each independently be selected from a substituted or unsubstituted $C_1$-$C_{60}$ alkyl group and a substituted or unsubstituted $C_6$-$C_{60}$ aryl group, but is not limited thereto.

In various embodiments, $R_{11}$ to $R_{17}$ in Formula 1 may each independently be selected from hydrogen, deuterium, —F, —Cl, —Br, —I, a $C_1$-$C_{20}$ alkyl group, a $C_1$-$C_{20}$ alkoxy group, a $C_3$-$C_{10}$ cycloalkyl group, and a $C_1$-$C_{10}$ heterocycloalkyl group;

a $C_1$-$C_{20}$ alkyl group, a $C_1$-$C_{20}$ alkoxy group, a $C_3$-$C_{10}$ cycloalkyl group, and a $C_1$-$C_{10}$ heterocycloalkyl group, each substituted with at least one selected from deuterium, —F, —Cl, —Br, and —I;

a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group;

a phenyl group, a naphthyl group, a phenanthrenyl group, an anthracenyl group, a triphenylenyl group, a pyrenyl group, a chrysenyl group, a pyrdinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from deuterium, —F, —Cl, —Br, —I, a $C_1$-$C_{20}$ alkyl group, a $C_1$-$C_{20}$ alkoxy group, a phenyl group, a naphthyl group, and —Si($Q_{11}$)($Q_{12}$)($Q_{13}$); and a phenyl group, a naphthyl group, a phenanthrenyl group, an anthracenyl group, a triphenylenyl group, a pyrenyl group, a chrysenyl group, a pyrdinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from a $C_1$-$C_{20}$ alkyl group, a phenyl group, and a naphthyl group, each substituted with at least one selected from deuterium, —F, —Cl, —Br, and —I;

two adjacent groups selected from $R_{11}$ to $R_{17}$ may be optionally linked to each other to form a saturated or unsaturated ring;

at least one of $R_{15}$ and $R_{17}$ may be selected from a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group;

a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from deuterium, —F, —Cl, —Br, —I, a $C_1$-$C_{20}$ alkyl group, a $C_1$-$C_{20}$ alkoxy group, a phenyl group, and a naphthyl group; and a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from a $C_1$-$C_{20}$ alkyl group, a phenyl group, and a naphthyl group, each substituted with at least one selected from deuterium, —F, —Cl, —Br, and —I; and $Q_{11}$ to $Q_{13}$ may each independently be selected from a methyl group, an ethyl group, and a phenyl group, but is not limited thereto.

In various embodiments, $R_{11}$ to $R_{17}$ in Formula 1 may each independently be selected from hydrogen, deuterium, —F, a methyl group, an ethyl group, an n-propyl group, an iso-propyl group, an n-butyl group, a sec-butyl group, an iso-butyl group, a tert-butyl group, an n-pentyl group, a methoxy group, an ethoxy group, a cyclopentyl group, a cyclohexyl group, and a cycloheptyl group;

a methyl group, an ethyl group, an n-propyl group, an iso-propyl group, an n-butyl group, a sec-butyl group, an iso-butyl group, a tert-butyl group, an n-pentyl group, a methoxy group, an ethoxy group, a cyclopentyl group, a cyclohexyl group, and a cycloheptyl group, each substituted with at least one selected from deuterium and —F;

a phenyl group, a naphthyl group, and a dibenzofuranyl group;

a phenyl group, a naphthyl group, and a dibenzofuranyl group, each substituted with at least one selected from deuterium, —F, a methyl group, an ethyl group, an n-propyl group, an iso-propyl group, an n-butyl group, a sec-butyl group, an iso-butyl group, a tert-butyl group, an n-pentyl group, a phenyl group, a naphthyl group, and —Si(CH$_3$)$_3$; and a phenyl group, a naphthyl group, and a dibenzofuranyl group, each substituted with at least one selected from a methyl group, an ethyl group, an n-propyl group, an iso-propyl group, an n-butyl group, a sec-butyl group, an iso-butyl group, a tert-butyl group, an n-pentyl group, a phenyl group, and a naphthyl group, each substituted with at least one selected from deuterium and —F;

two adjacent groups selected from $R_{11}$ to $R_{17}$ may be optionally linked to each other to form a saturated or unsaturated ring;

at least one of $R_{15}$ and $R_{17}$ may be selected from a phenyl group, a naphthyl group, and a dibenzofuranyl group;

a phenyl group, a naphthyl group, and a dibenzofuranyl group, each substituted with at least one selected from deuterium, —F, a methyl group, an ethyl group, an n-propyl group, an iso-propyl group, an n-butyl group, a sec-butyl group, an iso-butyl group, a tert-butyl group, an n-pentyl group, a phenyl group, and a naphthyl group; and a phenyl group, a naphthyl group, and a dibenzofuranyl group, each substituted with at least one selected from a methyl group, an ethyl group, an n-propyl group, an iso-propyl group, an n-butyl group, a sec-butyl group, an iso-butyl group, a tert-butyl group, an n-pentyl group, a phenyl group, and a naphthyl group, each substituted with at least one selected from deuterium and —F, but are not limited thereto.

In various embodiments, $R_{11}$ to $R_{17}$ in Formula 1 may each independently be selected from hydrogen, deuterium, —F, a methyl group, an ethyl group, an n-propyl group, an iso-propyl group, an iso-butyl group, a tert-butyl group, a cyclopentyl group, a cyclohexyl group, —CD$_3$, —CD$_2$H, —CDH$_2$, —CF$_3$, —CF$_2$H, —CFH$_2$, and groups represented by Formulae 5-1 to 5-19;

two adjacent groups selected from $R_{11}$ to $R_{17}$ may be optionally linked to each other to form a saturated or unsaturated ring; and at least one of $R_{15}$ and $R_{17}$ may be selected from groups represented by Formulae 5-1 to 5-19, but they are not limited thereto:

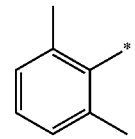

5-1

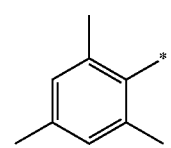

5-2

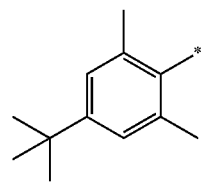

5-3

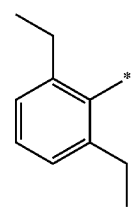

5-4

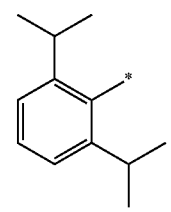

5-5

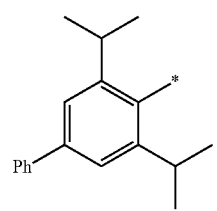

5-6

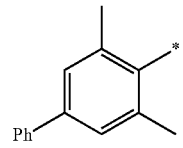

5-7

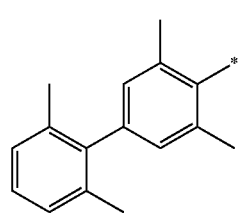

5-8

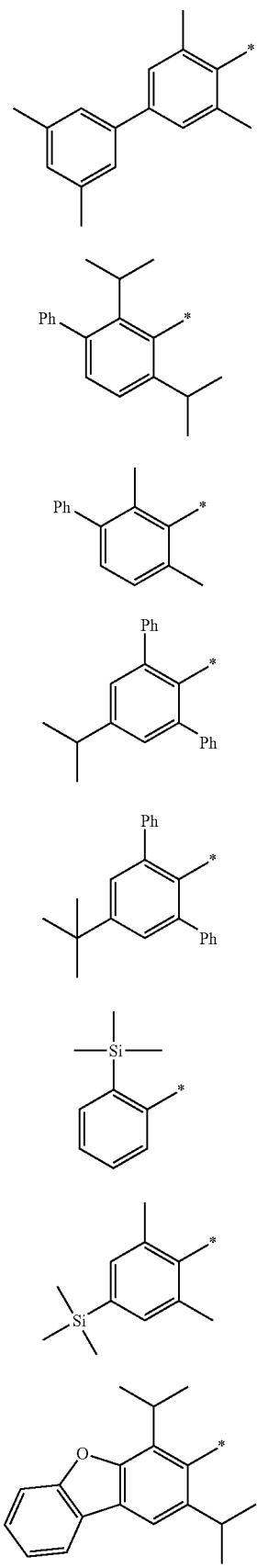

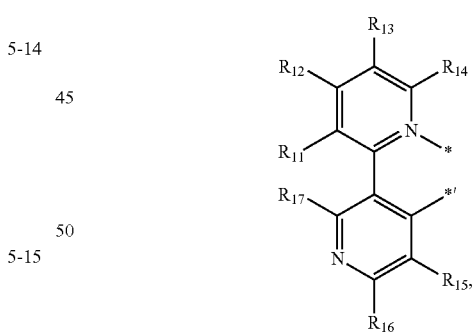

In Formulae 5-1 to 5-19,
* indicates a binding site to an adjacent atom; and
Ph indicates a phenyl group.

In various embodiments, $R_{11}$ to $R_{17}$ in Formula 1 may each independently be selected from hydrogen, deuterium, —F, a methyl group, an ethyl group, an n-propyl group, an iso-propyl group, an iso-butyl group, a tert-butyl group, a cyclopentyl group, a cyclohexyl group, —$CD_3$, —$CF_3$, and groups represented by Formulae 5-1 to 5-19;

two adjacent groups selected from $R_{11}$ to $R_{17}$ may be optionally linked to each other to form a saturated or unsaturated ring; and $R_{17}$ may be selected from groups represented by Formulae 5-1 to 5-19, but they are not limited thereto.

n in Formula 1 indicates the number of ligands represented by wherein * and *' each indicate a binding site to M in Formula 1. n in Formula 1 may be selected from 1, 2, and 3. When n in Formula 1 is 2 or more, the ligands may be identical to or different from each other.

For example, n in Formula 1 may be selected from 2 and 3, but is not limited thereto.

In various embodiments, M in Formula 1 may be Ir, and n may be 3, but is not limited thereto.

In various embodiments, M in Formula 1 may be Ir, and n may be 2, but is not limited thereto.

In various embodiments, M in Formula 1 may be Ir, and n may be 1, but is not limited thereto.

In various embodiments, M in Formula 1 may be Pt, and n may be 2, but is not limited thereto.

In various embodiments, M in Formula 1 may be Pt, and n may be 1, but M and n not limited thereto.

$L_{11}$ in Formula 1 may be selected from a monodentate ligand and a bidentate ligand.

For example, $L_{11}$ in Formula 1 may be selected from monodentate ligands, and $L_{11}$ may be selected from I⁻, Br⁻, Cl⁻, sulfide, nitrate, azide, hydroxide, cyanate, isocyanate, thiocyanate, water, acetonitrile, pyridine, ammonia, carbon monooxide, $P(Ph)_3$, $P(Ph)_2CH_3$, $PPh(CH_3)_2$, and $P(CH_3)_3$, but is not limited thereto.

In various embodiments, $L_{11}$ in Formula 1 may be selected from bidentate ligands, and $L_{11}$ may be selected from oxalate, acetylacetonate, picolinic acid, 2-(2-hydroxyphenyl)-pyridine, 2-phenylpyridine, 1,2-bis(diphenylphosphino)ethane, 1,1-bis(diphenylphosphino)methane, glycinate, ethylenediamine, 1,10-phenanthroline, and groups represented by Formulae 3-1 and 3-2, but is not limited thereto:

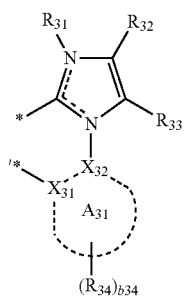

3-1

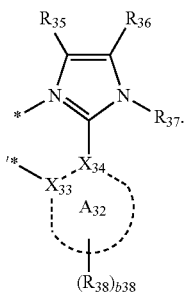

3-2

In Formulae 3-1 and 3-2, $A_{31}$ and $A_{32}$ may each independently be selected from a $C_6$-$C_{20}$ carbocyclic group and a $C_1$-$C_{20}$ heterocyclic group;

$X_{31}$ to $X_{34}$ may each independently be selected from a carbon atom (C) and a nitrogen atom (N);

$R_{31}$ to $R_{38}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_{31}$), —N($Q_{31}$)($Q_{32}$), and —Si($Q_{31}$)($Q_{32}$)($Q_{33}$); $R_{32}$ and $R_{33}$ may be optionally linked to each other to form a saturated or unsaturated ring; $R_{35}$ and $R_{36}$ may be optionally linked to each other to form a saturated or unsaturated ring;

b34 and b38 may each independently be selected from 1, 2, 3, 4, 5, and 6; and

* and *' each indicate a binding site to M in Formula 1.

For example, $A_{31}$ and $A_{32}$ in Formulae 3-1 and 3-2 may each independently be selected from a benzene, a naphthalene, an imidazole, a pyridine, a pyrimidine, a triazine, a quinoline, and an isoquinoline, but they are not limited thereto.

In various embodiments, $A_{31}$ and $A_{32}$ in Formulae 3-1 and 3-2 may be each independently a benzene, but they are not limited thereto.

For example, $R_{31}$ to $R_{38}$ in Formulae 3-1 and 3-2 may each independently be selected from hydrogen, deuterium, —F, —Cl, —Br, —I, a cyano group, a methyl group, an ethyl group, a phenyl group, and a naphthyl group, but they are not limited thereto.

m in Formula 1 indicates the number of groups $L_{11}$, and may be selected from 0, 1, 2, 3, and 4. When m is 2 or more, groups $L_{11}$ may be identical to or different from each other.

For example, m in Formula 1 may be 0, 1, and 2, but is not limited thereto.

In various embodiments, m in Formula 1 may be selected from 0 and 1, but is not limited thereto.

In various embodiments, m in Formula 1 may be 0, but is not limited thereto.

In various embodiments, the organometallic compound represented by Formula 1 may be selected from compounds represented by Formulae 1-1 to 1-4:

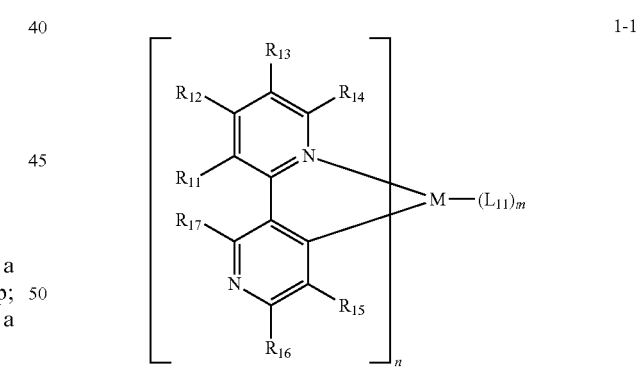

1-1

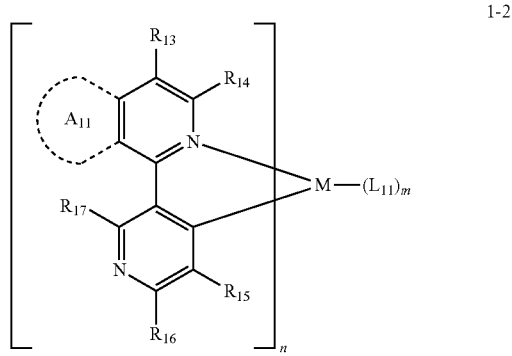

1-2

-continued

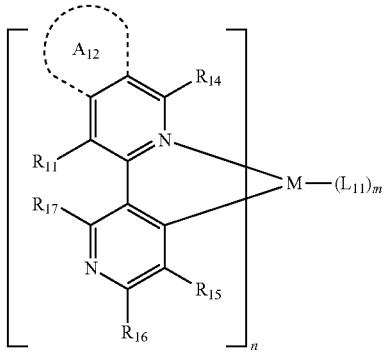

1-3

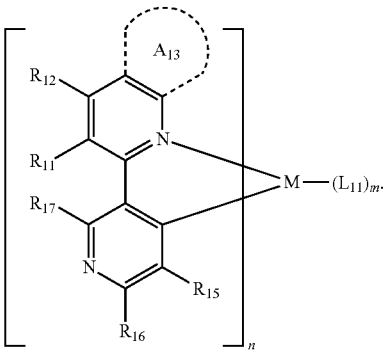

1-4

In Formulae 1-1 to 1-4, $A_{11}$ to $A_{13}$ may each independently be selected from substituted or unsubstituted $C_6$-$C_{20}$ carbocyclic groups; and M, $R_{11}$ to $R_{17}$, n, $L_{11}$, and m are the same as described in connection with Formula 1.

For example, $A_{11}$ to $A_{13}$ in Formulae 1-1 to 1-4 may each independently be selected from a cyclopentene, a cyclohexene, and a benzene, but they are not limited thereto.

In various embodiments, the organometallic compound represented by Formula 1 may be selected from compounds represented by Formulae 1-11 to 1-14:

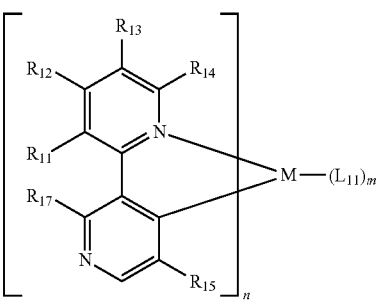

1-11

-continued

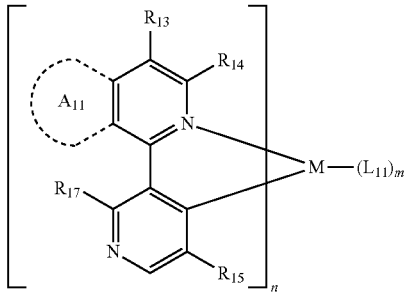

1-12

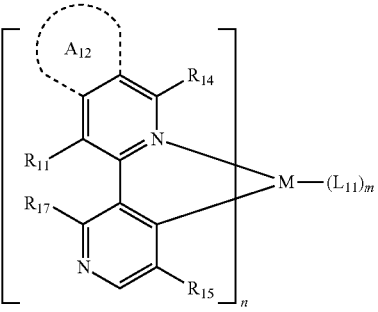

1-13

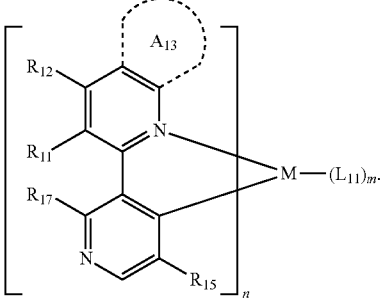

1-14

In Formulae 1-11 to 1-14, $A_{11}$ to $A_{13}$ may each independently be selected from a substituted or unsubstituted $C_6$-$C_{20}$ carbocyclic group;

M, $R_{11}$ to $R_{15}$, $R_{17}$, n, $L_{11}$, and m are the same as described in connection with Formula 1.

For example, $A_{11}$ to $A_{13}$ in Formulae 1-11 to 1-14 may each independently be selected from a cyclopentene, a cyclohexene, and a benzene, but they are not limited thereto.

In various embodiments, the organometallic compound represented by Formula 1 may be selected from compounds represented by Formulae 1-21 to 1-24:

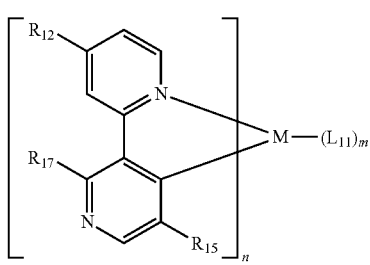

1-21

-continued

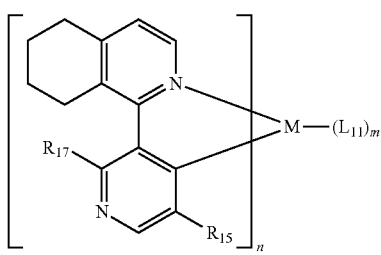

1-22

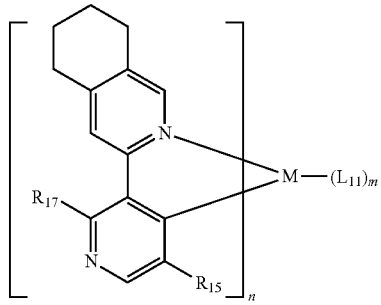

1-23

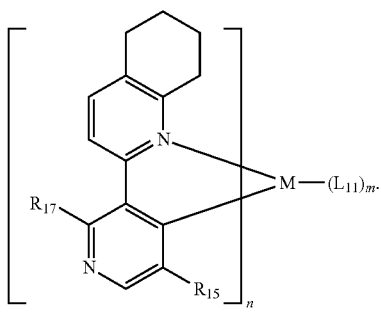

1-24

-continued

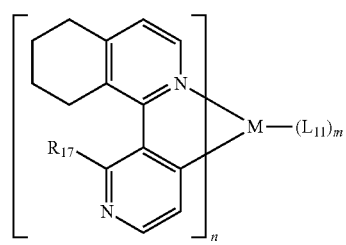

1-32

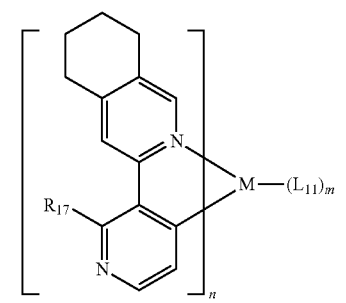

1-33

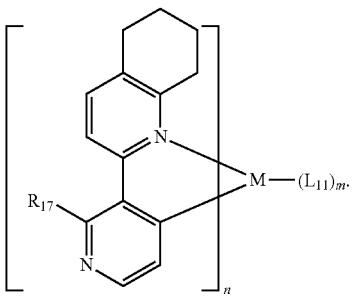

1-34

In Formulae 1-21 to 1-24,

M, $R_{12}$, $R_{15}$, $R_{17}$, n, $L_{11}$, and m are the same as described in connection with Formula 1.

For example, $R_{12}$, $R_{15}$, and $R_{17}$ in Formulae 1-21 to 1-24 may each independently be selected from hydrogen, deuterium, —F, a methyl group, an ethyl group, an n-propyl group, an iso-propyl group, an iso-butyl group, a tert-butyl group, a cyclopentyl group, a cyclohexyl group, —$CD_3$, —$CD_2H$, —$CDH_2$, —$CF_3$, —$CF_2H$, —$CFH_2$, and a group represented by one of Formulae 5-1 to 5-19; and at least one of $R_{15}$ and $R_{17}$ may be selected from groups represented by Formulae 5-1 to 5-19, but is not limited thereto.

In various embodiments, the organometallic compound represented by Formula 1 may be selected from groups represented by Formulae 1-31 to 1-34:

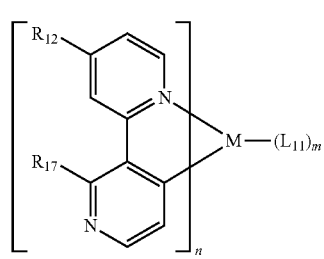

1-31

In Formulae 1-31 to 1-34,

M, $R_{12}$, $R_{17}$, n, $L_1$, and m are the same as described in connection with Formula 1.

For example, $R_{12}$ and $R_{17}$ in Formulae 1-31 to 1-34 may each independently be selected from hydrogen, deuterium, —F, a methyl group, an ethyl group, an n-propyl group, an iso-propyl group, an iso-butyl group, a tert-butyl group, a cyclopentyl group, a cyclohexyl group, —$CD_3$, —$CF_3$, and a group represented by one of Formulae 5-1 to 5-19; and $R_{17}$ may be selected from groups represented by Formulae 5-1 to 5-19, but is not limited thereto.

In various embodiments, the organometallic compound represented by Formula 1 may be selected from Compounds BD01 to BD12:

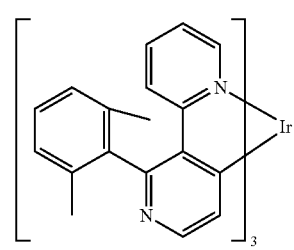

BD01

BD02 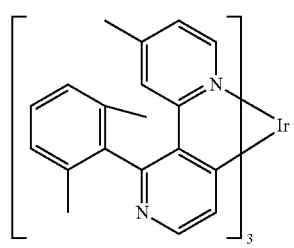
BD03 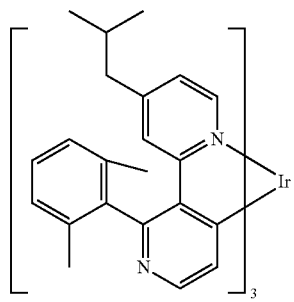
BD04 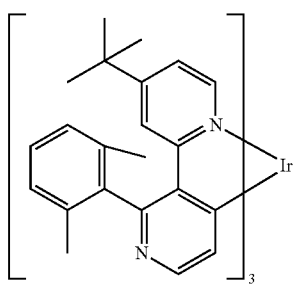
BD05 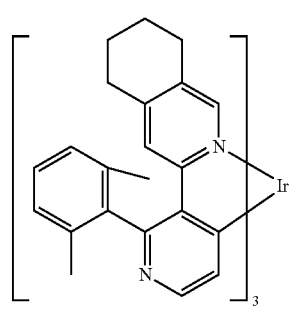
BD06 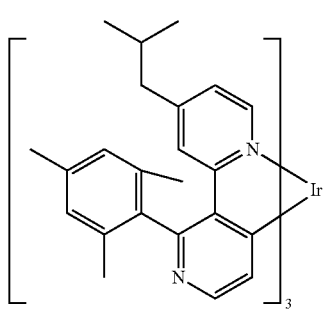
BD07 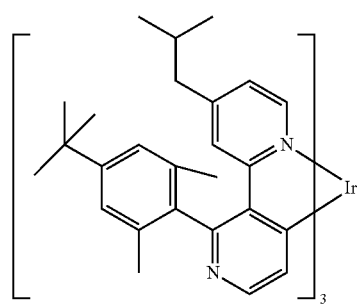
BD08 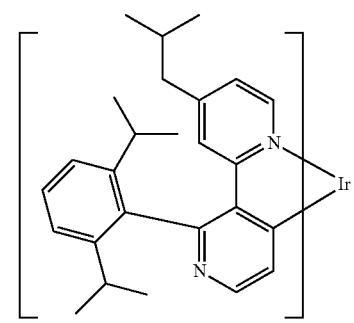
BD09 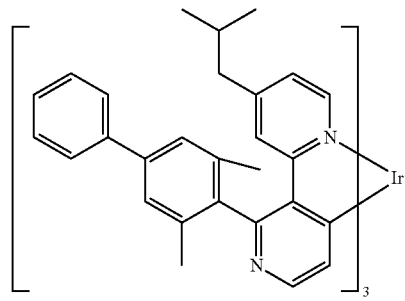
BD10 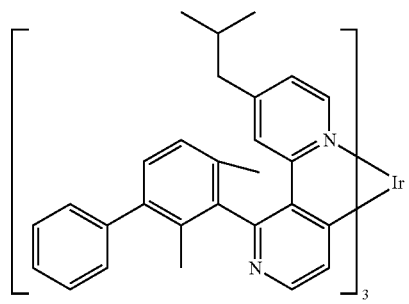
BD11 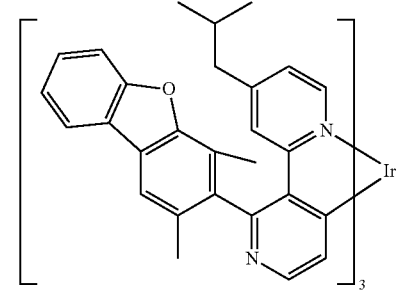

-continued

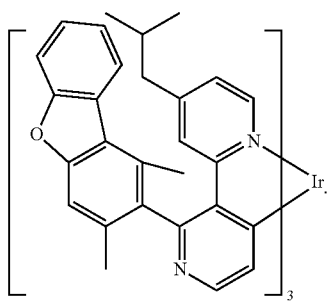

BD12

A maximum luminescent wavelength of the organometallic compound may be in a range of 420 nanometers (nm) to 480 nm, for example, 440 nm to 465 nm.

While not wishing to be bound by theory, it is understood that when the maximum luminescent wavelength is 480 nm or lower, an organic light-emitting device emitting blue light may be obtained.

The organometallic compound represented by Formula 1 may necessarily have a substituent having a large steric hindrance, such as an aryl group, in a pyridine ring. While not wishing to be bound by theory, it is understood that due to the inclusion of such a substituent, the organometallic compound may provide high thermal stability. Accordingly, an organic light-emitting device including the organometallic compound represented by Formula 1 may have improved lifespan.

Since the organometallic compound represented by Formula 1 may necessarily have a substituent having a large steric hindrance, such as an aryl group, in a pyridine ring, it is believed that, when the organometallic compound is deposited, aggregation may be suppressed and accordingly, the organometallic compound may be deposited in a uniform ratio with respect to an emission layer, for example, a host. Accordingly, an organic light-emitting device including the organometallic compound represented by Formula 1 may prevent exciton-quenching that occurs due to aggregation, thereby having improved efficiency.

Regarding the organometallic compound represented by Formula 1, like Formula 1', a non-coordinated nitrogen atom may be located in a para-position with respect to a metal atom. The organometallic compound may provide a high quantum yield and a short excited state lifespan.

Formula 1'

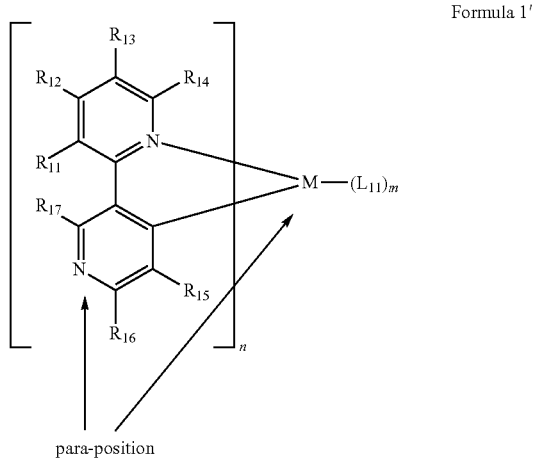

Due to the presence of the substituent having large steric hindrance, such as an aryl group, of the organometallic compound represented by Formula 1, a torsion strain between ring X1 and ring X2 illustrated in Formula 1" may be substantially reduced. Accordingly, an organic light-emitting device including the organometallic compound represented by Formula 1 may have improved driving voltage, current efficiency, and lifespan characteristics.

Formula 1"

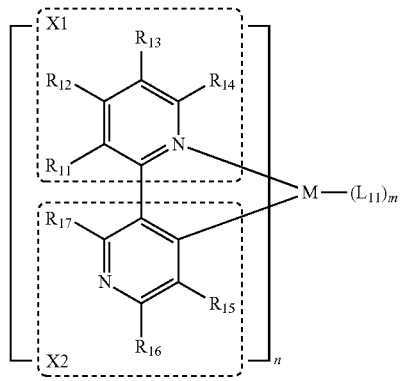

Meanwhile, an organometallic compound that necessarily has —F, for example, bis[2-(4,6-difluorophenyl)pyridinato-$C^2$, N](picolinato)iridium(III)(Flrpic) or tris[2-(4,6-difluorophenyl)pyridinato-$C^2$,N]iridium(III) is known to be unstable. However, since the organometallic compound represented by Formula 1 does not necessarily include —F, the organometallic compound may have stability.

A synthesis method for the organometallic compound represented by Formula 1 may be easily understood by one of ordinary skill in the art by referring to Synthesis Example.

Accordingly, the organometallic compound represented by Formula 1 is suitable for use in an organic layer of an organic light-emitting device, for example, a dopant of an emission layer constituting the organic layer. Thus, another aspect provides an organic light-emitting device including:

a first electrode;

a second electrode; and an organic layer disposed between the first electrode and the second electrode, wherein the organic layer includes an emission layer, and wherein the organometallic compound is represented by Formula 1.

Due to the inclusion of the organic layer including the organometallic compound represented by Formula 1, an organic light-emitting device having high efficiency, long lifespan and high color purity may be obtained.

The organometallic compound represented by Formula 1 may be used between a pair of electrodes of an organic light-emitting device. For example, the organometallic compound represented by Formula 1 may be included in the emission layer. In this regard, the organometallic compound acts as a dopant, and the emission layer may further include a host. The emission layer may emit red light, green light, or blue light.

The expression that "(an organic layer) includes an organometallic compound" as used herein may include an embodiment in which "(an organic layer) includes identical organometallic compounds represented by Formula 1 and an embodiment in which (an organic layer) includes two or more different organometallic compounds represented by Formula 1.

For example, the organic layer may include, as the organometallic compound, only Compound 1. In this regard, Compound 1 may be included in an emission layer of the organic light-emitting device. In some embodiments, the organic layer may include, as the organometallic compound, Compound 1 and Compound 2. In this regard, Compound 1 and Compound 2 may be included in an identical layer (for example, Compound 1 and Compound 2 may all be included in an emission layer).

The first electrode may be an anode, which is a hole injection electrode, and the second electrode may be a cathode, which is an electron injection electrode, or the first electrode may be a cathode, which is an electron injection electrode, or the second electrode may be an anode, which is a hole injection electrode.

For example, the first electrode may be an anode, and the second electrode may be a cathode, and the organic layer may include:

i) a hole transport region that is disposed between the first electrode and the emission layer, wherein the hole transport region includes at least one selected from a hole injection layer, a hole transport layer, and an electron blocking layer, and ii) an electron transport region that is disposed between the emission layer and the second electrode, wherein the electron transport region includes at least one selected from a hole blocking layer, an electron transport layer, and an electron injection layer.

The term "organic layer" as used herein refers to a single layer and/or a plurality of layers between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked.

A substrate may be additionally disposed below the first electrode 11 or above the second electrode 19. For use as the substrate, any substrate that is used in general organic light-emitting devices may be used, and the substrate may be a glass substrate having excellent mechanical strength, thermal stability, transparency, surface smoothness, ease of handling, and water-resistance, or a transparent plastic substrate.

The first electrode 11 may be formed by depositing or sputtering a material for forming the first electrode 11 on the substrate. The first electrode 11 may be an anode. The material for the first electrode 11 may be selected from materials with a high work function to facilitate hole injection. The first electrode 11 may be a reflective electrode, a semi-transmissive electrode, or a transmissive electrode. The material for the first electrode 11 may be an indium tin oxide (ITO), indium zinc oxide (IZO), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/hole transport layer/electron blocking layer, which are sequentially stacked in this stated order from the first electrode 11.

When the hole transport region includes a hole injection layer (HIL), the hole injection layer may be formed on the first electrode 11 by using any one of various methods, for example, vacuum deposition, spin coating, casting, or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

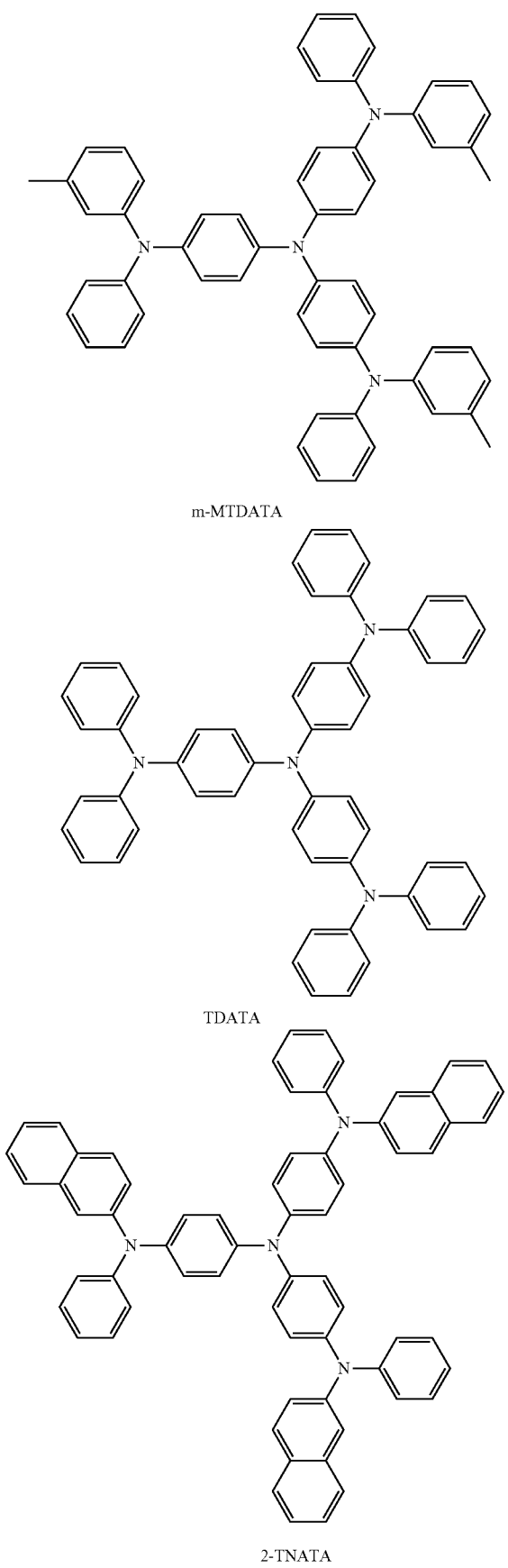
m-MTDATA
TDATA
2-TNATA
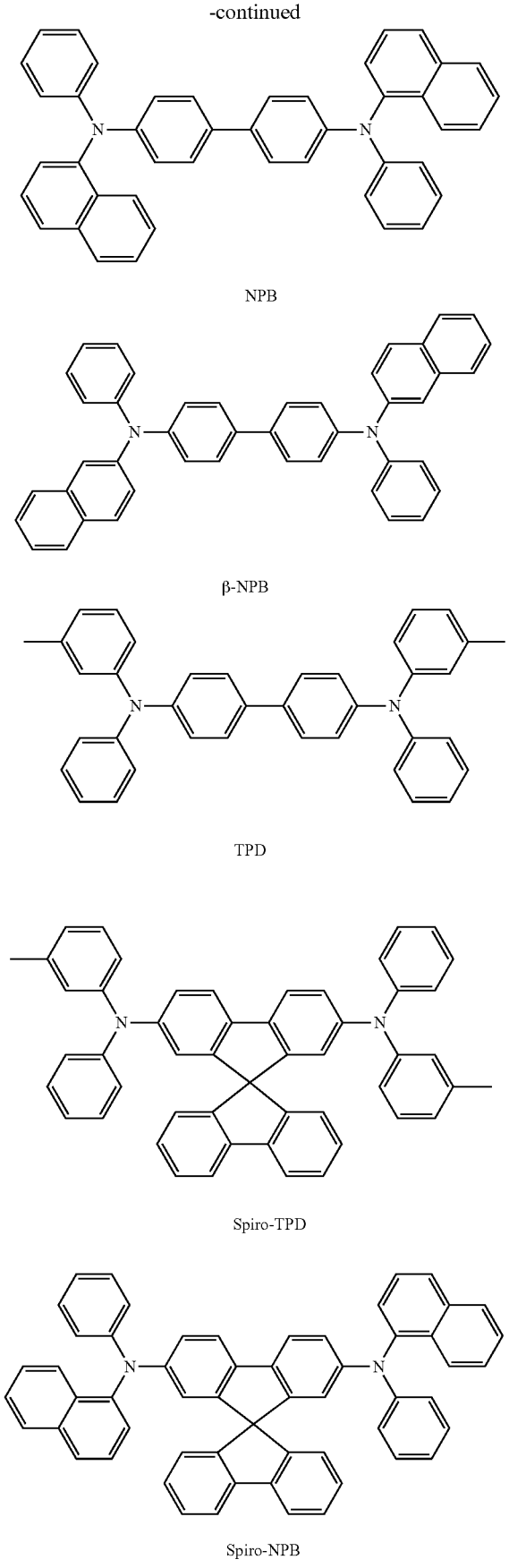
NPB
β-NPB
TPD
Spiro-TPD
Spiro-NPB

-continued

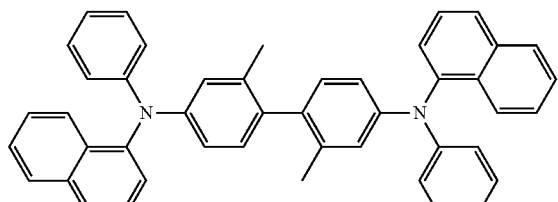

methylated NPB

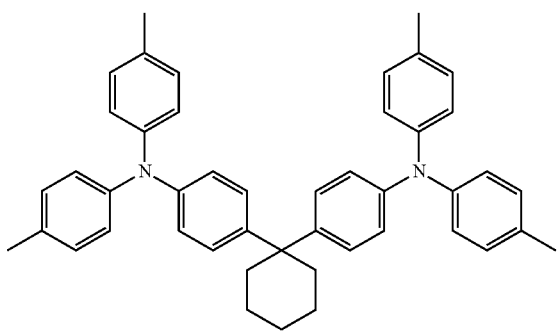

TAPC

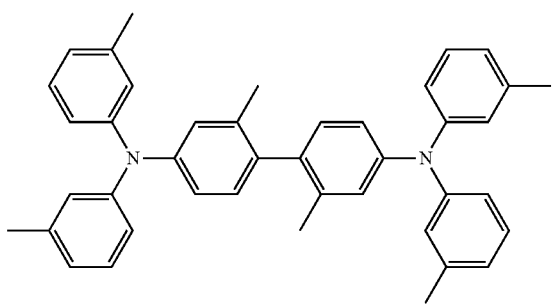

HMTPD

Formula 201

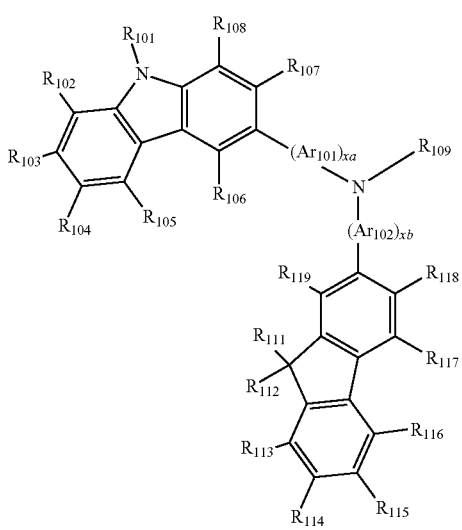

-continued

Formula 202

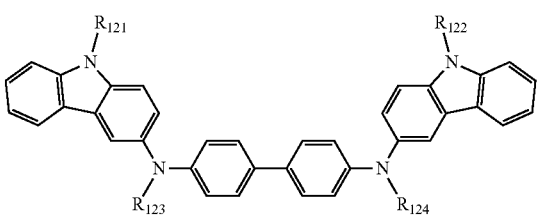

Ar$_{101}$ and Ar$_{102}$ in Formula 201 may each independently be selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_3$-C$_{10}$ cycloalkenyl group, a C$_2$-C$_{10}$ heterocycloalkyl group, a C$_2$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent non-aromatic condensed polycyclic group, and a monovalent non-aromatic condensed heteropolycyclic group.

xa and xb in Formula 201 may each independently be an integer of 0 to 5, or 0, 1 or 2. For example, xa may be 1 and xb may be 0, but xa and xb are not limited thereto.

R$_{101}$ to R$_{108}$, R$_{111}$ to R$_{119}$, and R$_{121}$ to R$_{124}$ in Formulae 201 and 202 may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group (for example, a methyl group, an ethyl group, a propyl group, a butyl group, a pentyl group, a hexyl group, and so on), or a C$_1$-C$_{10}$ alkoxy group (for example, a methoxy group, an ethoxy group, a propoxy group, a butoxy group, a pentoxy group, and so on);

a C$_1$-C$_{10}$ alkyl group or a C$_1$-C$_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group and a $C_1$-$C_{10}$ alkoxy group, but they are not limited thereto.

$R_{109}$ in Formula 201 may be a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A below, but is not limited thereto:

Formula 201A

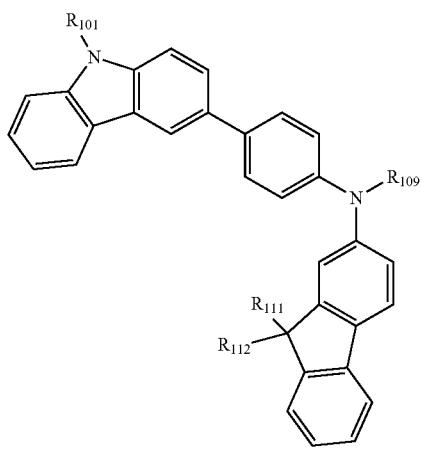

$R_{101}$, $R_{111}$, $R_{112}$, and $R_{109}$ in Formula 201A may be understood by referring to the description provided herein.

For example, the compound represented by Formula 201, and the compound represented by Formula 202 may include compounds HT1 to HT20 illustrated below, but are not limited thereto.

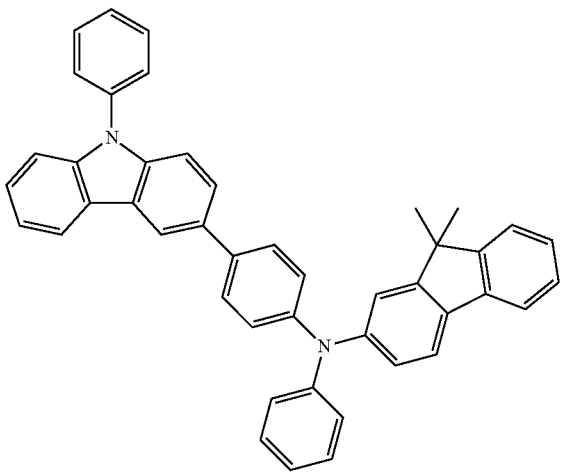
HT1

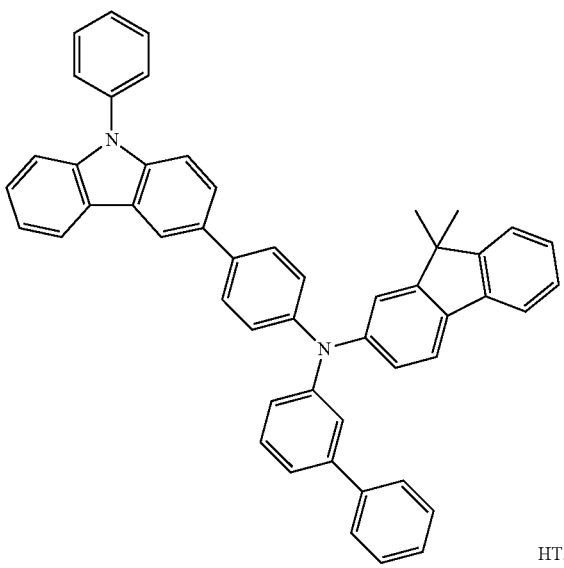
HT2

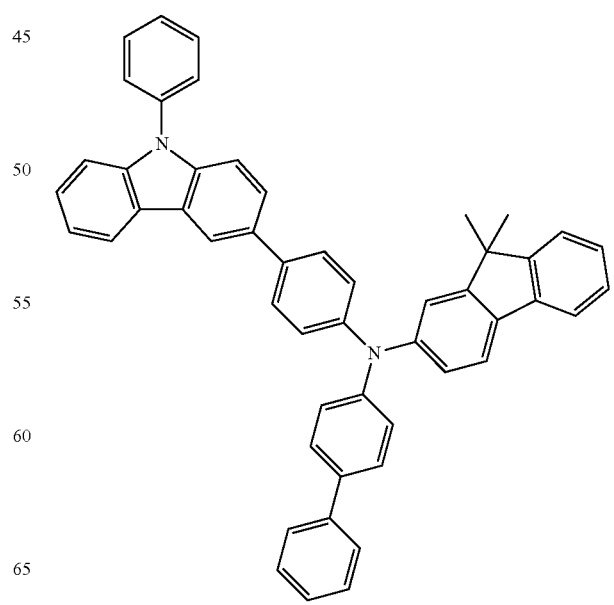
HT3

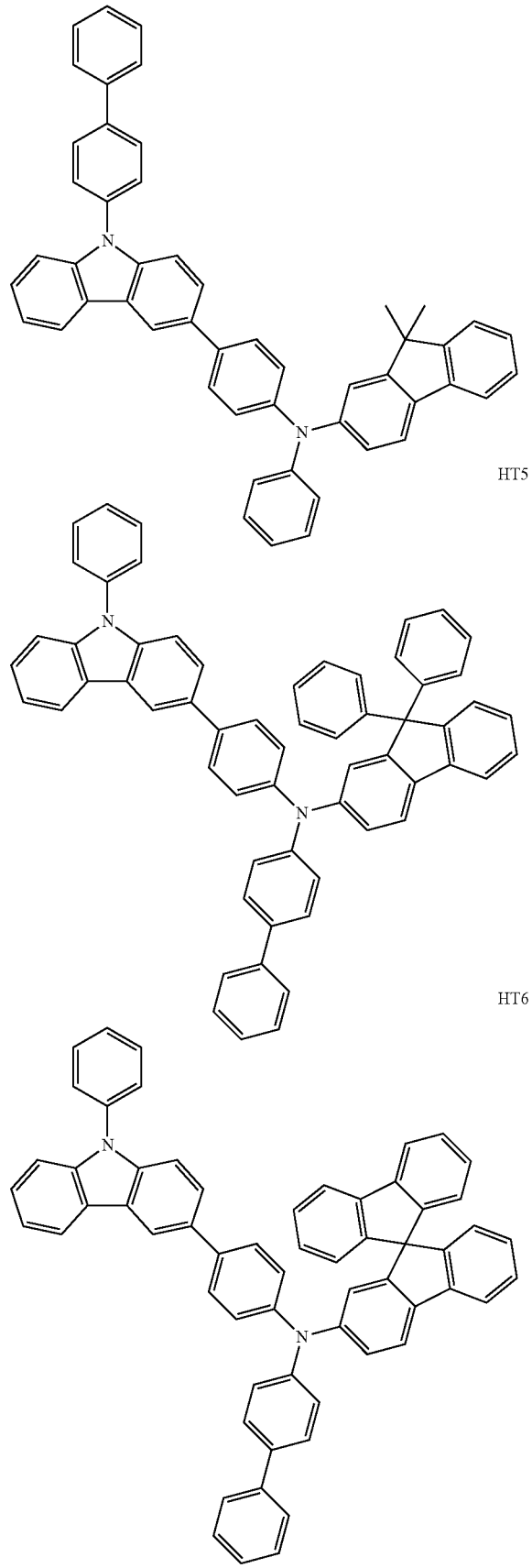
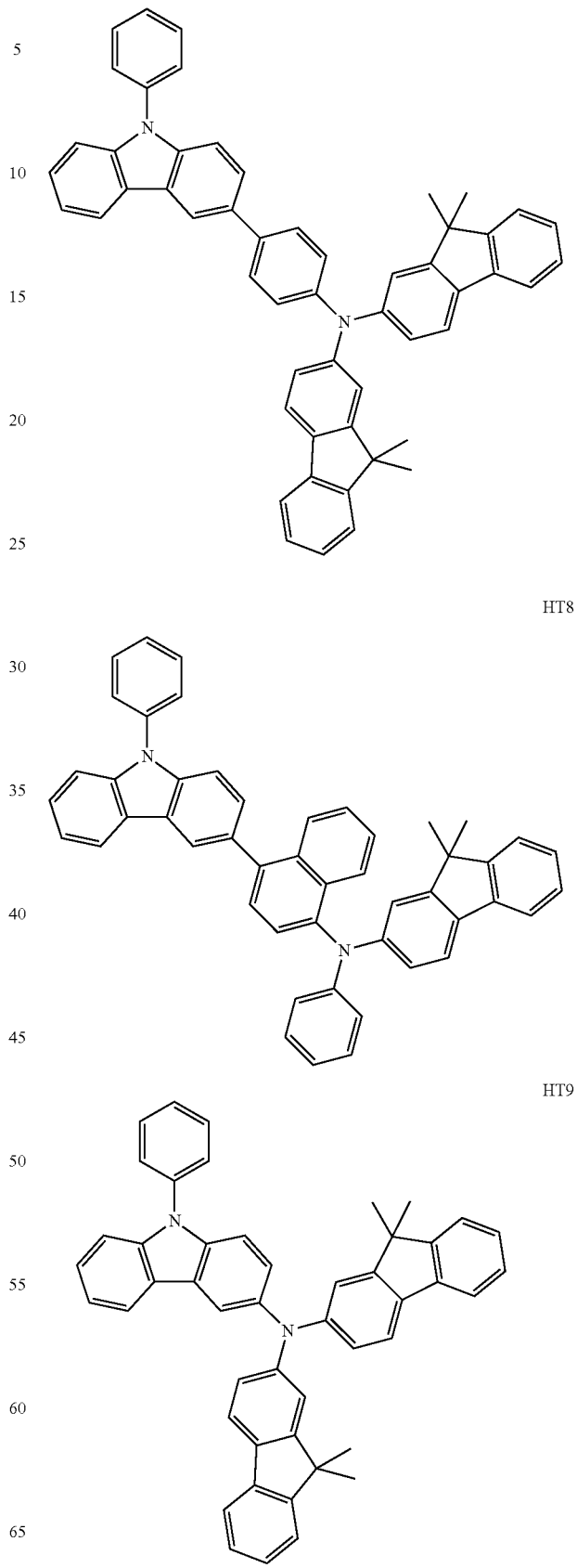

-continued
HT10
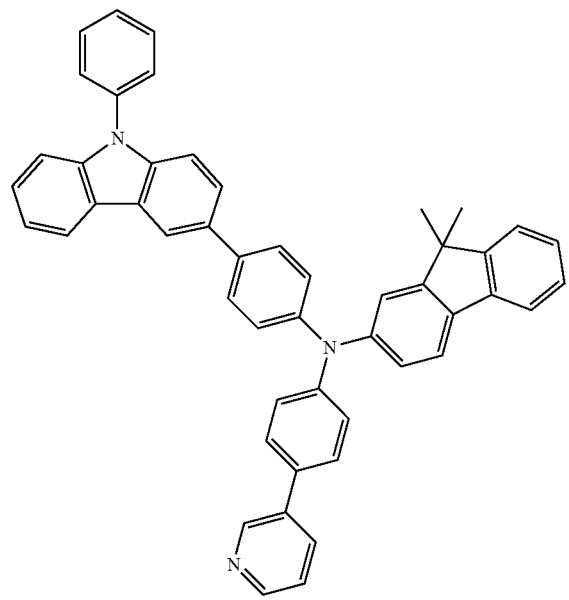
HT11
HT12
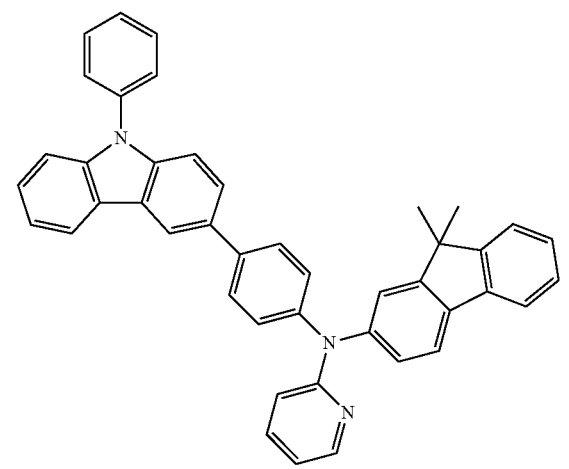
HT13
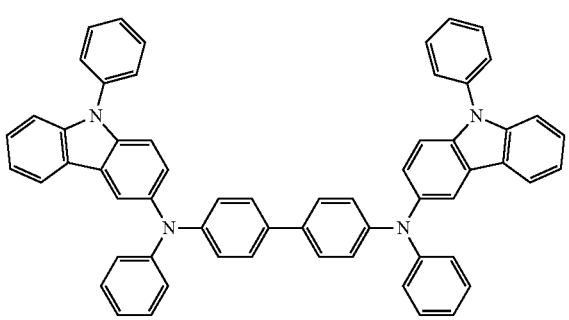
HT14
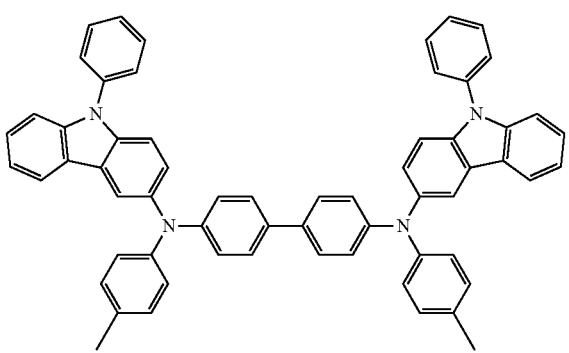
HT15
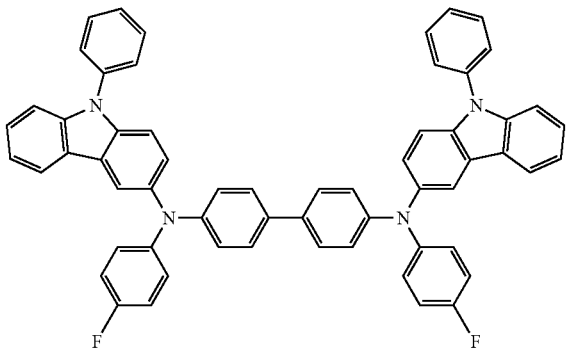
HT16
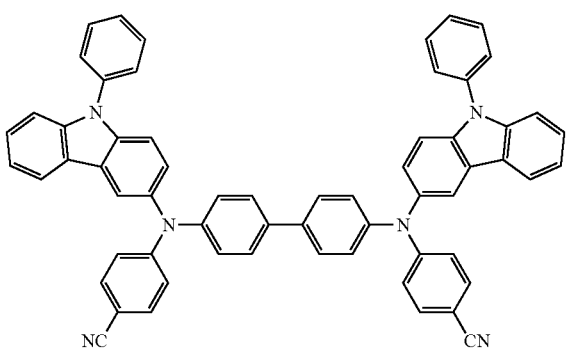

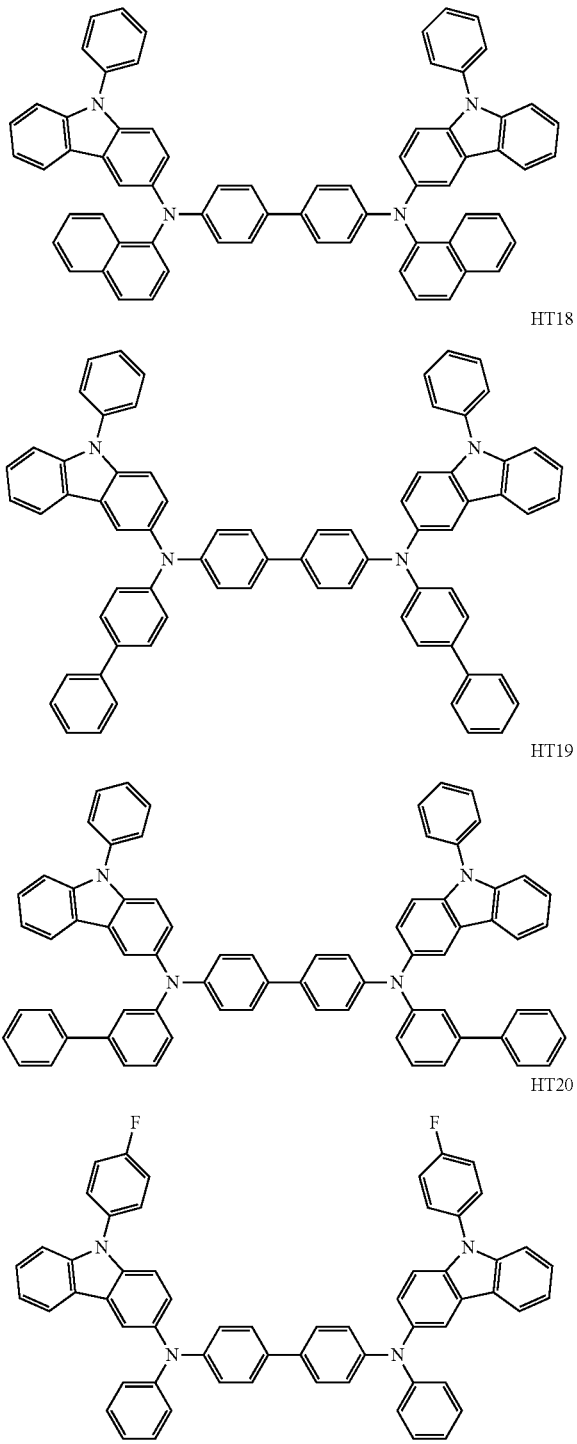

HT17

HT18

HT19

HT20

A thickness of the hole transport region may be in a range of about 100 Å to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thicknesses of the hole transport region, the hole injection layer and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenium oxide; and a cyano group-containing compound, such as Compound HT-D1 or Compound HT-D2 below, but are not limited thereto.

Compound HT-D1

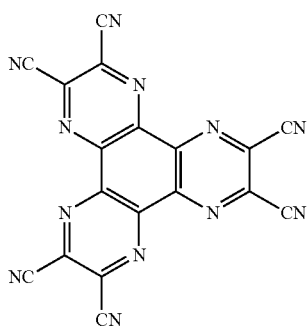

F4-TCNQ

Compound HT-D2

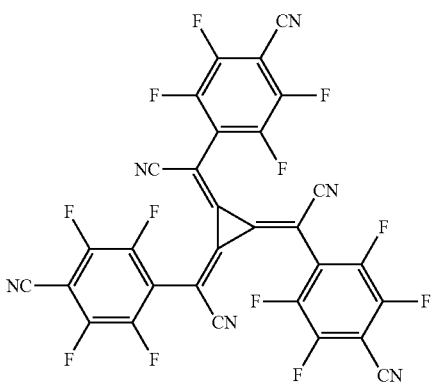

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer (EML) may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The emission layer may include a host and a dopant.

The host may include at least one selected from CBP, CDBP, TCP, and mCP:

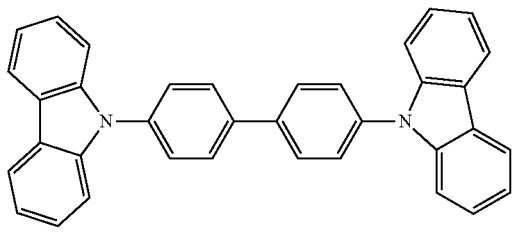

CBP

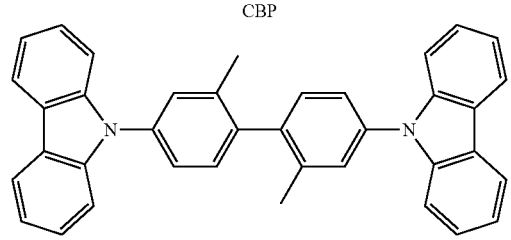

CDBP

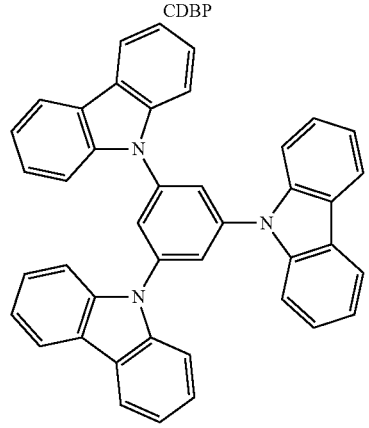

TCP

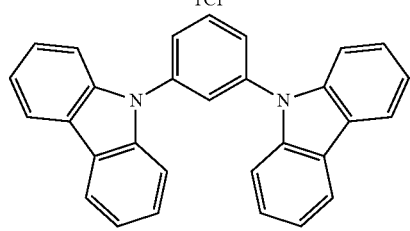

mCP

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include the organometallic compound represented by Formula 1 as a dopant.

When the emission layer includes a host and a dopant, an amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP and Bphen, but may also include other materials.

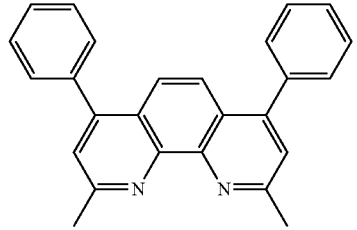

BCP

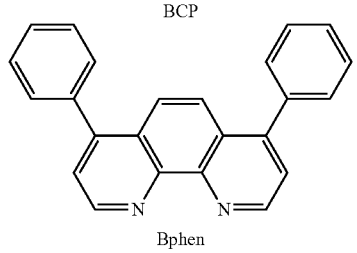

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, Balq, TAZ, and NTAZ.

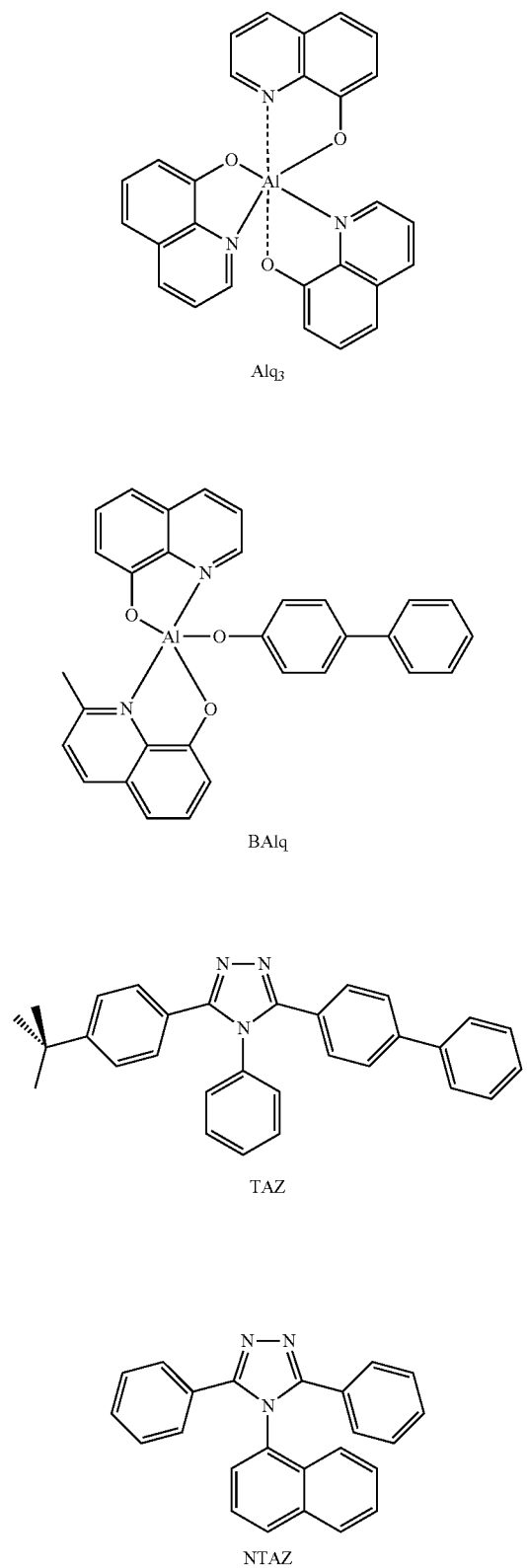
Alq₃
BAlq
TAZ
NTAZ
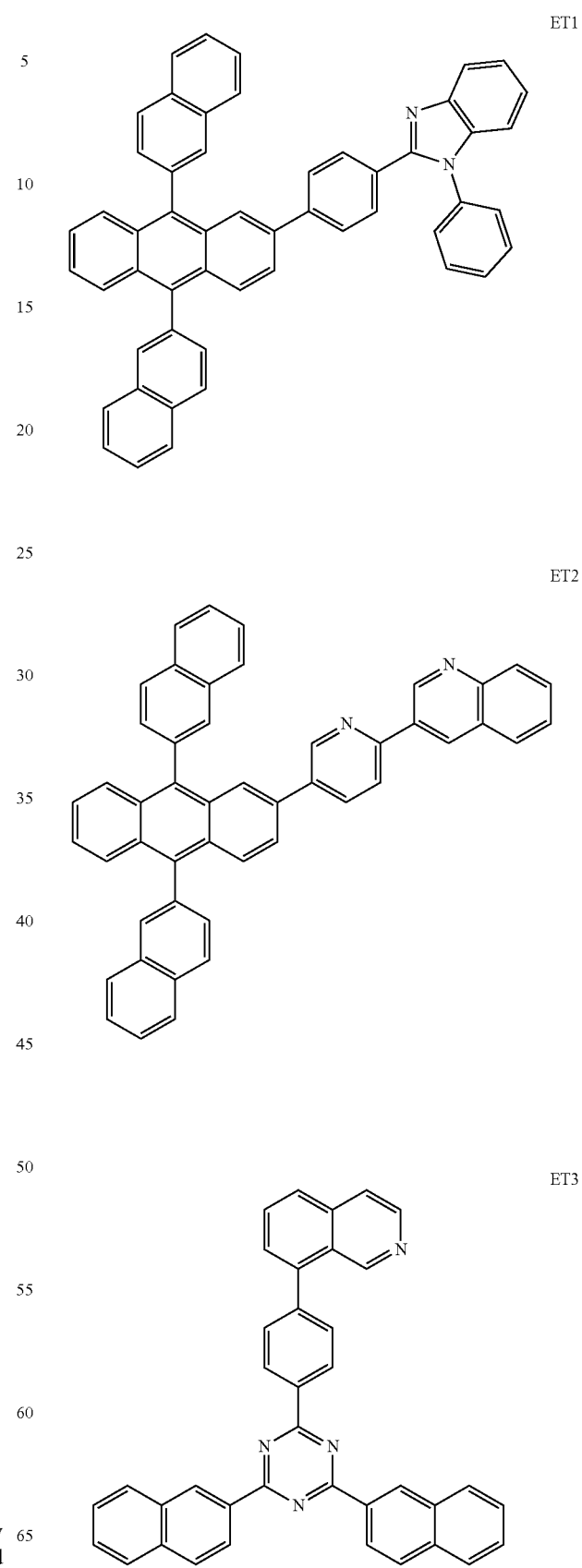
ET1
ET2
ET3
In some embodiments, the electron transport layer may include at least one of ET1 and ET19, but are not limited thereto:

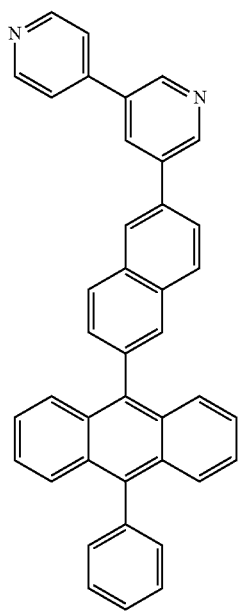
ET4
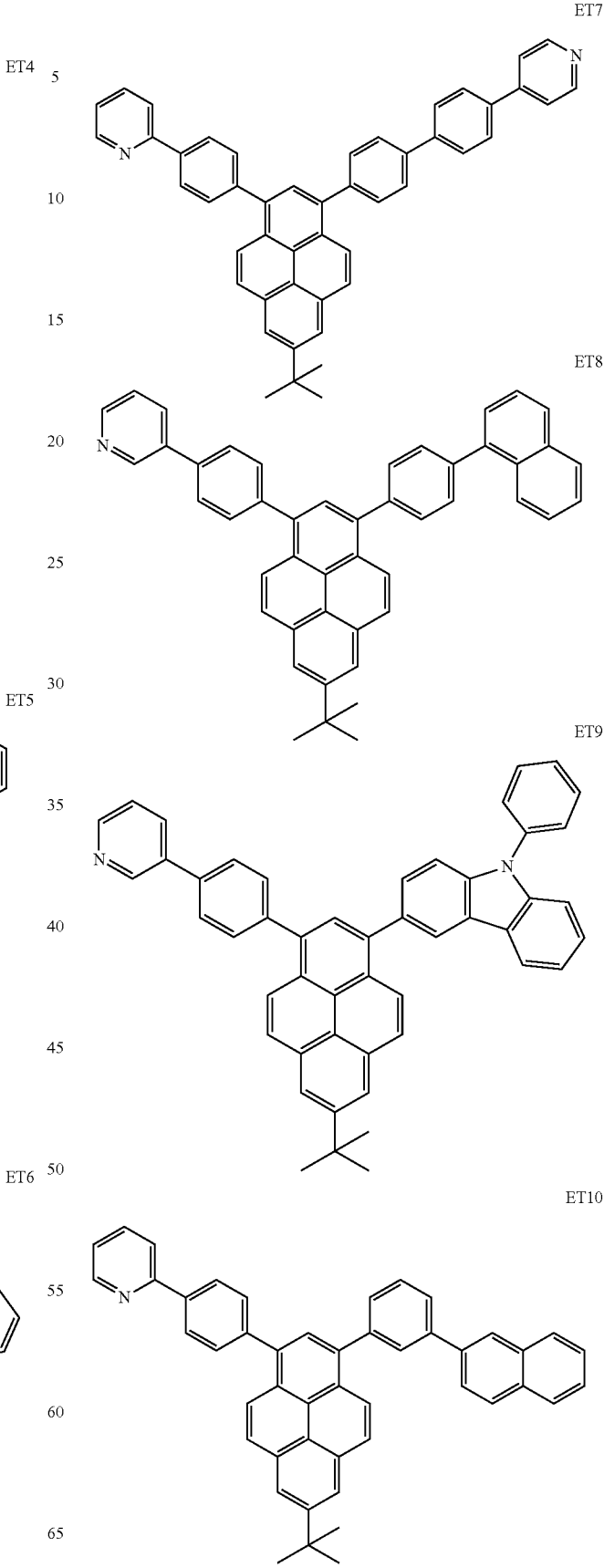
ET5
ET6
ET7
ET8
ET9
ET10

ET11
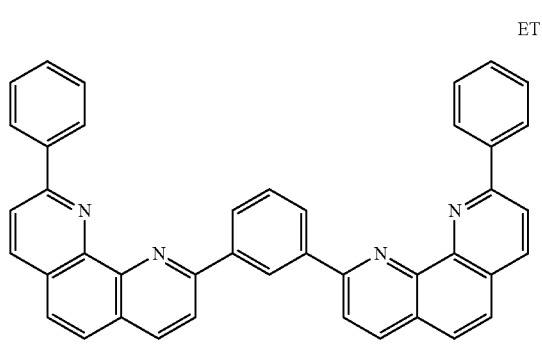
ET14
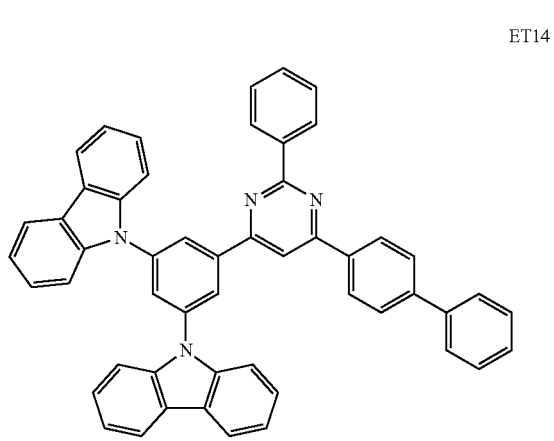
ET12
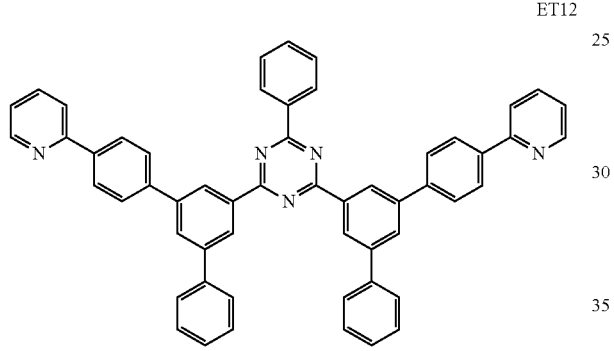
ET15
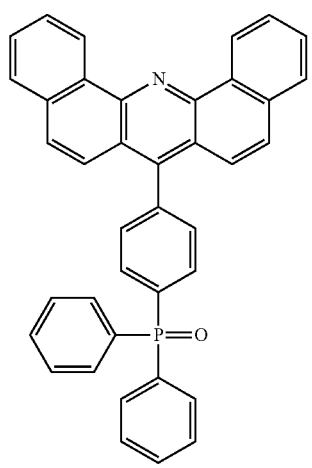
ET13
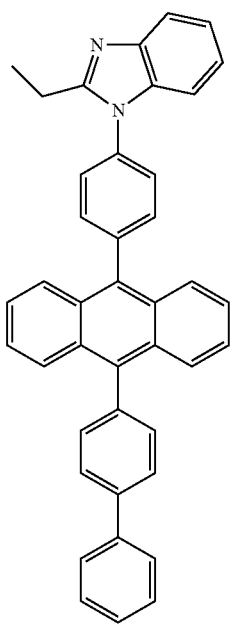
ET16
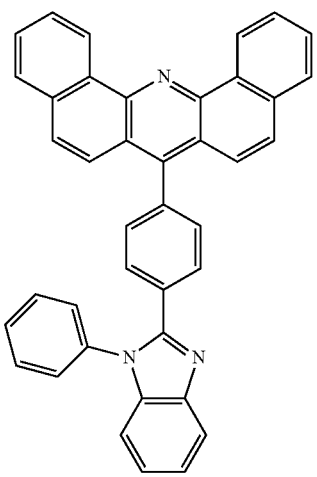

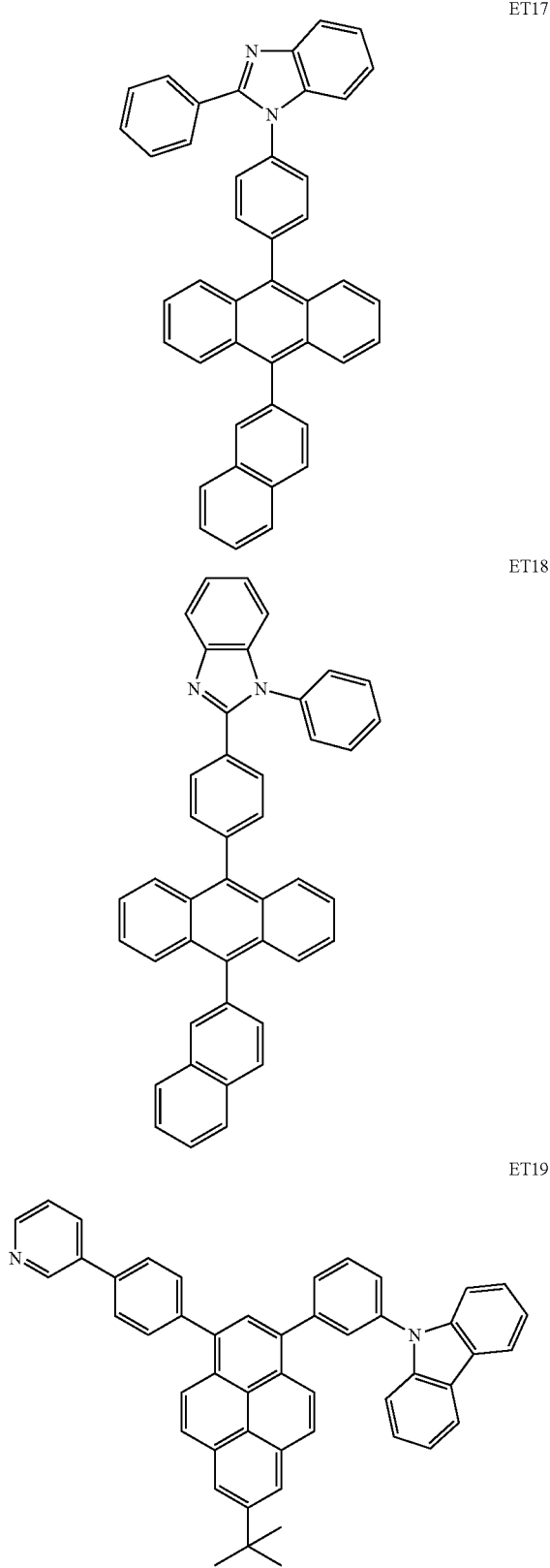

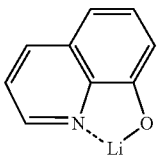

ET-D1

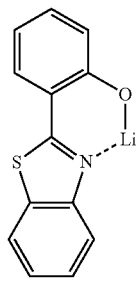

ET-D2

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The Li complex may include, for example, Compound ET-D1 (lithium quinolate, LiQ) or ET-D2. The Li complex may include, for example, Compound ET-D1 (lithium quinolate, LiQ) or ET-D2.

The electron transport layer may include an electron injection layer (EIL) that promotes flow of electrons from the second electrode 19 thereinto.

The electron injection layer may include at least one selected from, LiF, NaCl, CsF, Li$_2$O, BaO, and LiQ.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{30}$ alkyl group as used herein refers to a linear or branched aliphatic hydrocarbon monovalent group having 1 to 60 carbon atoms. Detailed examples thereof are a methyl group, an ethyl group, a propyl group, an iso-butyl group, a sec-butyl group, a tert-butyl group, a pentyl group, an iso-amyl group, and a hexyl group.

A $C_1$-$C_{30}$ alkoxy group as used herein refers to a monovalent group represented by —$OA_{101}$ (wherein $A_{101}$ is the $C_1$-$C_{30}$ alkyl group). Detailed examples thereof are a methoxy group, an ethoxy group, and an iso-propyloxy group.

A $C_2$-$C_{30}$ alkenyl group as used herein refers to a hydrocarbon group formed by introducing at least one carbon double bond in the middle or at the terminal of the $C_2$-$C_{30}$ alkyl group. Detailed examples thereof are an ethenyl group, a propenyl group, and a butenyl group.

A $C_2$-$C_{60}$ alkynyl group as used herein refers to a hydrocarbon group formed by substituting at least one carbon triple bond in the middle or at the terminal of the $C_2$-$C_{30}$ alkyl group. Detailed examples thereof are an ethynyl group and a propynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms. Detailed examples thereof are a tetrahydrofuranyl group, and a tetrahydrothiophenyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group.

A $C_1$-$C_{10}$ heterocycloalkenyl group as used herein refers to a monovalent monocyclic group that has at least one heteroatom selected from N, O, P, and S as a ring-forming atom, 1 to 10 carbon atoms, and at least one double bond in its ring. Examples of the $C_1$-$C_{10}$ heterocycloalkenyl group are a 2,3-dihydrofuranyl group and a 2,3-dihydrothiophenyl group.

A $C_6$-$C_{60}$ aryl group as used herein refers to a monovalent group having a carbocyclic aromatic system having 6 to 60 carbon atoms. Detailed examples of the $C_6$-$C_{30}$ aryl group are a phenyl group, a naphthyl group, an anthracenyl group, a phenanthrenyl group, a pyrenyl group, and a chrysenyl group. When the $C_6$-$C_{60}$ aryl group includes two or more rings, the rings may be fused to each other.

A $C_6$-$C_{60}$ aryloxy group as used herein refers to a monovalent group represented by —$OA_{101}$ (wherein $A_{101}$ is the $C_6$-$C_{60}$ aryl group), and a detailed example thereof is a phenoxy group.

A $C_6$-$C_{60}$ arylthio group as used herein refers to a monovalent group represented by —$SA_{101}$ (wherein $A_{101}$ is the $C_6$-$C_{60}$ aryl group), and a detailed example thereof is a phenylthio group.

A $C_1$-$C_{60}$ heteroaryl group as used herein refers to a monovalent carbocylic aromatic system having at least one heteroatom selected from N, O, P, and S as a ring-forming atom and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group includes two or more rings, the rings may be fused to each other.

A monovalent non-aromatic condensed polycyclic group as used herein refers to a monovalent group that has two or more rings condensed to each other, only carbon atoms as a ring forming atom, and which is non-aromatic in the entire molecular structure. Detailed example of the monovalent non-aromatic condensed polycyclic group is a fluorenyl group.

A monovalent non-aromatic condensed heteropolycyclic group as used herein refers to a monovalent group that has two or more rings condensed to each other, has a heteroatom selected from N, O P, and S, other than carbon atoms, as a ring forming atom, and which is non-aromatic in the entire molecular structure. Detailed example of the monovalent non-aromatic condensed heteropolycyclic group is a carbazolyl group.

The $C_6$-$C_{20}$ carbocyclic group as used herein refers to an aliphatic or aromatic group having 6 to 20 carbon atoms. Detailed examples of the $C_6$-$C_{20}$ carbocyclic group are a cyclohexane, a cyclohexene, a benzene, a naphthalene. When the $C_6$-$C_{20}$ carbocyclic group includes two or more rings, the rings may be fused to each other.

The $C_1$-$C_{20}$ heterocyclic group as used herein refers to an aliphatic or aromatic group having a heteroatom selected from N, O, P, and S and 1 to 20 carbon atoms. Detailed examples of the $C_1$-$C_{20}$ heterocyclic group are a pyrrolidine, a piperidine, tetrahydrofuran, a pyrrole, a furan, and a thiophene. When the $C_1$-$C_{20}$ heterocyclic group includes two or more rings, the rings may be fused to each other.

At least one of substituents of the substituted $C_1$-$C_{30}$ alkyl group, substituted $C_2$-$C_{30}$ alkenyl group, substituted $C_2$-$C_{30}$ alkynyl group, substituted $C_1$-$C_{30}$ alkoxy group, substituted $C_3$-$C_{60}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{30}$ aryl group, substituted $C_6$-$C_{60}$ aryloxy group, substituted $C_6$-$C_{60}$ arylthio group, substituted $C_1$-$C_{30}$ heteroaryl group, substituted monovalent non-aromatic condensed polycyclic group, substituted monovalent non-aromatic condensed heteropolycyclic group, and substituted $C_6$-$C_{20}$ carbocyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and $C_1$-$C_{30}$ alkoxy group;

a $C_1$-$C_{60}$ alkyl group, a $C_2$-$C_{30}$ alkenyl group, a $C_2$-$C_{30}$ alkynyl group, and $C_1$-$C_{30}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, and a monovalent non-aromatic condensed heteropolycyclic group; and a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and $C_1$-$C_{30}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, and a monovalent non-aromatic condensed heteropolycyclic group.

For example, at least one of substituents of the substituted $C_1$-$C_{30}$ alkyl group, substituted $C_2$-$C_{30}$ alkenyl group, substituted $C_2$-$C_{30}$ alkynyl group, substituted $C_1$-$C_{30}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{30}$ aryl group, substituted $C_6$-$C_{60}$ aryloxy group, substituted $C_6$-$C_{60}$ arylthio group, substituted $C_1$-$C_{30}$ heteroaryl group, substituted monovalent non-aromatic condensed polycyclic group, substituted monovalent non-aromatic condensed heteropolycyclic group, and substituted $C_6$-$C_{20}$ carbocyclic group may be selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and $C_1$-$C_{30}$ alkoxy group;

a $C_1$-$C_{30}$ alkyl group, a $C_2$-$C_{30}$ alkenyl group, a $C_2$-$C_{30}$ alkynyl group, and $C_1$-$C_{30}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, and a monovalent non-aromatic condensed heteropolycyclic group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group and an imidazopyridinyl group, each substituted with at least one selected from a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, and an imidazopyridinyl group, each substituted with at least one selected from a cyclopentyl group, a cyclohexyl group, a cycloheptyl group, a cyclooctyl group, a cyclopentenyl group, a cyclohexenyl group, a cycloheptenyl group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and $C_1$-$C_{30}$ alkoxy group, a $C_3$-$C_{10}$ cycloalkyl group, a $C_1$-$C_{10}$ heterocycloalkyl group, a $C_3$-$C_{60}$ cycloalkenyl group, a $C_1$-$C_{10}$ heterocycloalkenyl group, a $C_6$-$C_{30}$ aryl group, a $C_6$-$C_{30}$ aryloxy group, a $C_6$-$C_{30}$ arylthio group, a $C_1$-$C_{30}$ heteroaryl group, a monovalent non-aromatic condensed polycyclic group, and a monovalent non-aromatic condensed heteropolycyclic group.

When a group containing a specified number of carbon atoms is substituted with any of the groups listed in the preceding paragraph, the number of carbon atoms in the resulting "substituted" group is defined as the sum of the carbon atoms contained in the original (unsubstituted) group and the carbon atoms (if any) contained in the substituent. For example, when the term "substituted $C_1$-$C_{30}$ alkyl" refers to a $C_1$-$C_{30}$ alkyl group substituted with $C_6$-$C_{30}$ aryl group, the total number of carbon atoms in the resulting aryl substituted alkyl group is $C_7$-$C_{60}$.

Hereinafter, a compound and an organic light-emitting device including the compound according to one or more embodiments of the present disclosure will be described in more detail with reference to Synthesis Examples and Examples. However, these examples are for illustrative purposes only and are not intended to limit the scope of the present disclosure. The term "B was used instead of A" used in describing Synthesis Examples may refer to a molar equivalent of 'A' being identical to a molar equivalent of 'B'.

EXAMPLES

Synthesis Example 1: Synthesis of Compound BD01

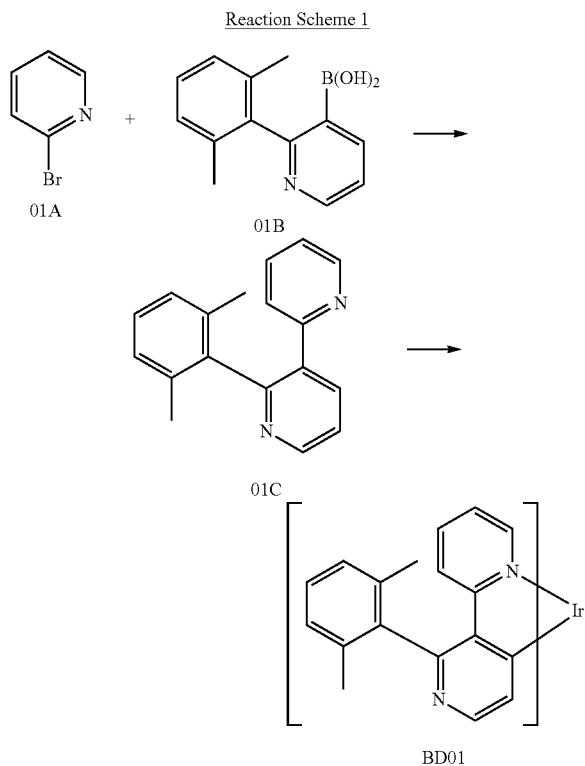

1) Synthesis of Intermediate 01C

Material 01A (63.3 millimoles (mmol)), Material 01B (75.9 mmol), Pd(PPh$_3$)$_4$ (3.2 mmol), K$_2$CO$_3$ (189.9 mmol), 200 milliliters (mL) of 1,4-dioxane, and 67 mL of distilled water were added to a 1.0 liter (L) reaction container, and the mixed solution was refluxed in a nitrogen atmosphere for 12 hours. After the reaction is completed, the resulting solution was cooled to room temperature and was subjected to an extraction process using dichloromethane and distilled water. An organic layer collected therefrom was washed twice with distilled water, dried by using magnesium sulfate (MgSO$_4$), and then a solvent was removed therefrom. The crude products obtained therefrom were purified by silica gel column chromatography (using ethyl acetate and n-hexane as an eluent), thereby completing the preparation of Intermediate 01C (26.58 mmol).

LC-MS (m/z): 261.23 [M+1]

2) Synthesis of Compound BD01

Ir(COD)$_2$BF$_4$ (5.32 mmol), 01C (26.58 mmol), and glycerol were added together to a reaction container, and the mixed solution was refluxed in a nitrogen atmosphere for 12 hours. After the reaction is completed, the resulting solution was cooled to room temperature, and was subjected to an extraction process using dichloromethane and distilled water. An organic layer collected therefrom was washed twice with distilled water, dried by using magnesium sulfate (MgSO$_4$), and then a solvent was removed therefrom. The crude products obtained therefrom were purified by silica gel column chromatography (using ethyl acetate and n-hexane as an eluent), thereby completing the preparation of Compound BD01 (1.1 mmol, yield: 20%).

MALDI-TOF(m/z): 970.28 [M+1]$^+$

Synthesis Example 2: Synthesis of Compound BD02

Compound BD02 (yield: 22%) was synthesized in the same manner according to Reaction Scheme 1, except that in synthesizing Compound BD01 of Reaction Scheme 1, Initial material 02A shown in Structural Formulae of Intermediates below was used instead of Initial material 01A.

MALDI-TOF(m/z): 1012.57 [M+1]$^+$

Synthesis Example 3: Synthesis of Compound BD03

Compound BD03 (yield: 20%) was synthesized in the same manner according to Reaction Scheme 1, except that in synthesizing Compound BD01 of Reaction Scheme 1, Initial material 03A shown in Structural Formulae of Intermediates below was used instead of Initial material 01A.

MALDI-TOF(m/z): 1138.23 [M+1]$^+$

Synthesis Example 4: Synthesis of Compound BD04

Compound BD04 (yield: 18%) was synthesized in the same manner according to Reaction Scheme 1, except that in synthesizing Compound BD01 of Reaction Scheme 1, Initial material 04A shown in Structural Formulae of Intermediates below was used instead of Initial material 01A.

MALDI-TOF(m/z): 1138.38 [M+1]$^+$

Synthesis Example 5: Synthesis of Compound BD05

Compound BD05 (yield: 15%) was synthesized in the same manner according to Reaction Scheme 1, except that in synthesizing Compound BD01 of Reaction Scheme 1, Initial material 05A shown in Structural Formulae of Intermediates below was used instead of Initial material 01A.

MALDI-TOF(m/z): 1132.87 [M+1]$^+$

Synthesis Example 6: Synthesis of Compound BD06

Compound BD06 (yield: 21%) was synthesized in the same manner according to Reaction Scheme 1, except that in synthesizing Compound BD01 of Reaction Scheme 1, Materials 03A and 06B shown in Structural Formulae of Intermediates below were used instead of Initial materials 01A and 01B, respectively.
MALDI-TOF(m/z): 1180.22 [M+1]$^+$

Synthesis Example 7: Synthesis of Compound BD07

Compound BD07 (yield: 21%) was synthesized in the same manner according to Reaction Scheme 1, except that in synthesizing Compound BD01 of Reaction Scheme 1, Materials 03A and 07B shown in Structural Formulae of Intermediates below were used instead of Initial materials 01A and 01B, respectively.
MALDI-TOF(m/z): 1306.46 [M+1]$^+$

Synthesis Example 8: Synthesis of Compound BD08

Compound BD08 (yield: 19%) was synthesized in the same manner according to Reaction Scheme 1, except that in synthesizing Compound BD01 of Reaction Scheme 1, Materials 03A and 08B shown in Structural Formulae of Intermediates below were used instead of Initial materials 01A and 01B, respectively.
MALDI-TOF(m/z): 1306.22 [M+1]$^+$

Synthesis Example 9: Synthesis of Compound BD09

Compound BD09 (yield: 15%) was synthesized in the same manner according to Reaction Scheme 1, except that in synthesizing Compound BD01 of Reaction Scheme 1, Materials 03A and 09B shown in Structural Formulae of Intermediates below were used instead of Initial materials 01A and 01B, respectively.
MALDI-TOF(m/z): 1366.82 [M+1]

Synthesis Example 10: Synthesis of Compound BD10

Compound BD10 (yield: 16%) was synthesized in the same manner according to Reaction Scheme 1, except that in synthesizing Compound BD01 of Reaction Scheme 1, Materials 03A and 10B shown in Structural Formulae of Intermediates below were used instead of Initial materials 01A and 01B, respectively.
MALDI-TOF(m/z): 1366.52 [M+1]$^+$

Synthesis Example 11: Synthesis of Compound BD11

Compound BD11 (yield: 12%) was synthesized in the same manner according to Reaction Scheme 1, except that in synthesizing Compound BD01 of Reaction Scheme 1, Materials 03A and 11B shown in Structural Formulae of Intermediates below were used instead of Initial materials 01A and 01B, respectively.
MALDI-TOF(m/z): 1408.51 [M+1]$^+$

Synthesis Example 12: Synthesis of Compound BD12

Compound BD12 (yield: 13%) was synthesized in the same manner according to Reaction Scheme 1, except that in synthesizing Compound BD01 of Reaction Scheme 1, Materials 03A and 12B shown in Structural Formulae of Intermediates below were used instead of Initial materials 01A and 01B, respectively.
MALDI-TOF(m/z): 1408.26 [M+1]$^+$ Structural Formulae of Intermediates

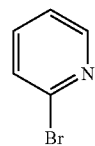

01A

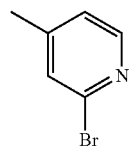

02A

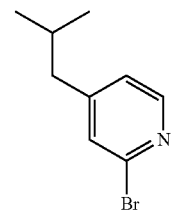

03A

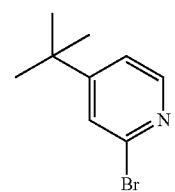

04A

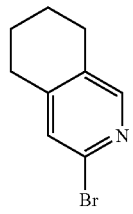

05A

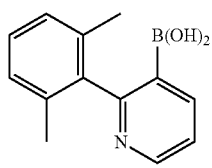

01B

-continued

06B
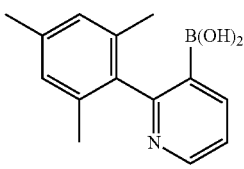

07B
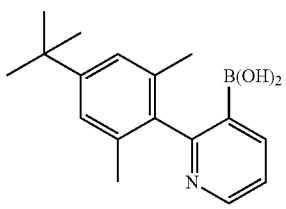

09B
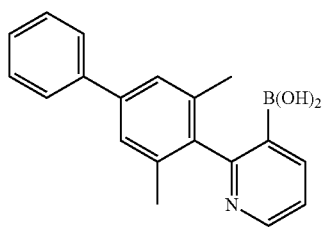

10B
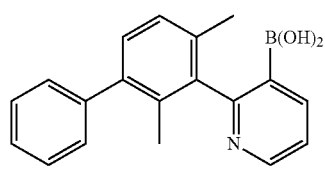

11B
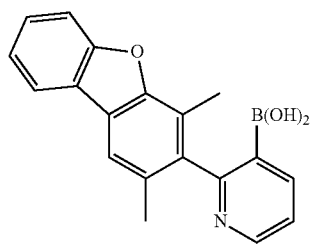

12B
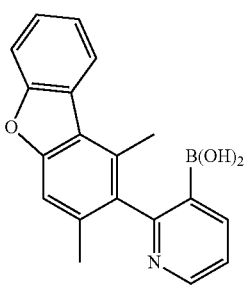

Evaluation Example 1: Evaluation of HOMO, LUMO, and $T_1$ Energy Levels of Compounds A, B, and BD01 to BD12

According to methods described in Table 1 below, HOMO, LUMO, and T1 energy levels of Compounds A, B and BD01 to BD12 were evaluated, and results are shown in Table 2 below.

TABLE 1

| | |
|---|---|
| HOMO energy level evaluation | Cyclic voltammetry (CV) (electrolyte: 0.1M $Bu_4NClO_4$/solvent: $CH_2Cl_2$/ electrode: 3 electrode system (working electrode: GC, standard electrode: Ag/AgCl, auxiliary electrode: Pt)) is used to draw a potential (Volts, V) - current (Amperes, A) graph regarding each compound. Based on reduction onset values of the graph, HOMO energy levels for each compound are calculated. |
| LUMO energy level evaluation | Each compound is diluted with $CHCl_3$ to a concentration of $1 \times 10^{-5}$ molar (M), and Shimadzu UV-350 Spectrometer is used to measure UV absorption spectrum of each compound at room temperature. LUMO energy levels for each compound are calculated using optical band gap (Eg) values of the edge of the absorption spectrum. |
| $T_1$ energy level evaluation | Each compound is diluted with $CH_2Cl_2$ to a concentration of 10 millimolar (mM), and ISC PC1 Spectrofluorometer equipped with Xenon light is used to measure photoluminescence spectrum of each compound at room temperature. $\lambda_{max}$ values measured therefrom are converted to electron Volts (eV) values. |

TABLE 2

| Compound | HOMO (eV) | LUMO (eV) | $T_1$ (eV) | $\lambda_{max}$ (nm) |
|---|---|---|---|---|
| A | -5.75 | -2.85 | 2.79 | 444 |
| B | -5.52 | -2.93 | 2.59 | 479 |
| BD01 | -5.68 | -3.09 | 2.62 | 473 |
| BD02 | -5.54 | -2.98 | 2.64 | 469 |
| BD03 | -5.52 | -2.94 | 2.65 | 468 |
| BD04 | -5.53 | -2.90 | 2.65 | 468 |
| BD05 | -5.42 | -2.73 | 2.66 | 466 |
| BD06 | -5.47 | -2.90 | 2.65 | 468 |
| BD07 | -5.47 | -2.95 | 2.65 | 468 |
| BD08 | -5.57 | -2.98 | 2.65 | 468 |
| BD09 | -5.56 | -2.98 | 2.64 | 470 |
| BD10 | -5.55 | -2.96 | 2.64 | 469 |
| BD11 | -5.68 | -2.99 | 2.65 | 468 |
| BD12 | -5.66 | -2.99 | 2.65 | 468 |

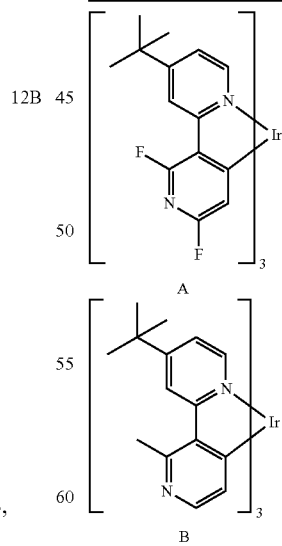

Referring to Table 2 above, it was confirmed that Compounds BD01 to BD12 had appropriate electric characteristics to be used as a material for manufacturing the organic light-emitting device.

Example 1

A glass substrate on which an indium tin oxide (ITO) electrode (i.e., a first electrode or an anode) was formed to a thickness of 1,500 Angstroms (Å) was ultrasonically washed with distilled water. After the washing using distilled water was completed, the glass substrate was ultrasonically washed with a solvent, such as isopropyl alcohol, acetone, and methanol, and dried. The glass substrate was transported to a plasma washing machine to be cleaned using oxygen plasma for 5 minutes, and then, transported to be mounted on a vacuum depositor.

Compound HT3 was vacuum-deposited on the ITO electrode of the glass substrate to form a first hole injection layer (HIL) having a thickness of 3,500 Å, and Compound HT-D1 was vacuum-deposited on the first HIL to form a second HIL having a thickness of 300 Å. Subsequently, TAPC was vacuum-deposited on the second HIL to form an electron blocking layer (EBL) having a thickness of 100 Å, thereby forming a hole transport region.

mCP as a host and Compound BD01 (7 percent by weight (wt %)) as a dopant were co-deposited on the hole transport region to form an emission layer (EML) having a thickness of 300 Å.

Compound ET3 was vacuum-deposited on the EML to form an electron transport layer (ETL) having a thickness of 250 Å, and ET-D1 (Liq) was deposited on the ETL to form an electron injection layer (EIL) having a thickness of 5 Å. Then, Al was deposited on the EIL to form a second electrode (i.e., a cathode) having a thickness of 1,000 Å, thereby completing the manufacture of an organic light-emitting device.

Example 2

An organic light-emitting device was manufactured in the same manner as in Example 1, except that in forming the EML, Compound BD02 was used instead of Compound BD01 as the dopant.

Example 3

An organic light-emitting device was manufactured in the same manner as in Example 1, except that in forming the EML, Compound BD03 was used instead of Compound BD01 as the dopant.

Example 4

An organic light-emitting device was manufactured in the same manner as in Example 1, except that in forming the EML, Compound BD04 was used instead of Compound BD01 as the dopant.

Example 5

An organic light-emitting device was manufactured in the same manner as in Example 1, except that in forming the EML, Compound BD05 was used instead of Compound BD01 as the dopant.

Example 6

An organic light-emitting device was manufactured in the same manner as in Example 1, except that in forming the EML, Compound BD06 was used instead of Compound BD01 as the dopant.

Example 7

An organic light-emitting device was manufactured in the same manner as in Example 1, except that in forming the EML, Compound BD07 was used instead of Compound BD01 as the dopant.

Example 8

An organic light-emitting device was manufactured in the same manner as in Example 1, except that in forming the EML, Compound BD08 was used instead of Compound BD01 as the dopant.

Example 9

An organic light-emitting device was manufactured in the same manner as in Example 1, except that in forming the EML, Compound BD09 was used instead of Compound BD01 as the dopant.

Example 10

An organic light-emitting device was manufactured in the same manner as in Example 1, except that in forming the EML, Compound BD10 was used instead of Compound BD01 as the dopant.

Example 11

An organic light-emitting device was manufactured in the same manner as in Example 1, except that in forming the EML, Compound BD11 was used instead of Compound BD01 as the dopant.

Example 12

An organic light-emitting device was manufactured in the same manner as in Example 1, except that in forming the EML, Compound BD12 was used instead of Compound BD01 as the dopant.

Comparative Example 1

An organic light-emitting device was manufactured in the same manner as in Example 1, except that in forming the EML, Compound A was used instead of Compound BD01 as the dopant.

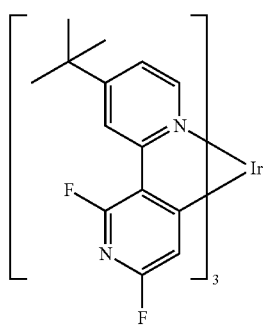

A

Comparative Example 2

An organic light-emitting device was manufactured in the same manner as in Example 1, except that in forming the EML, Compound B was used instead of Compound BD01 as the dopant.

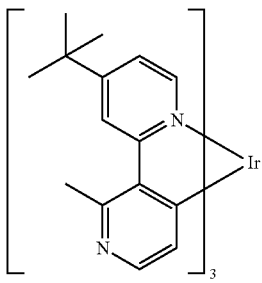

Figure 2:
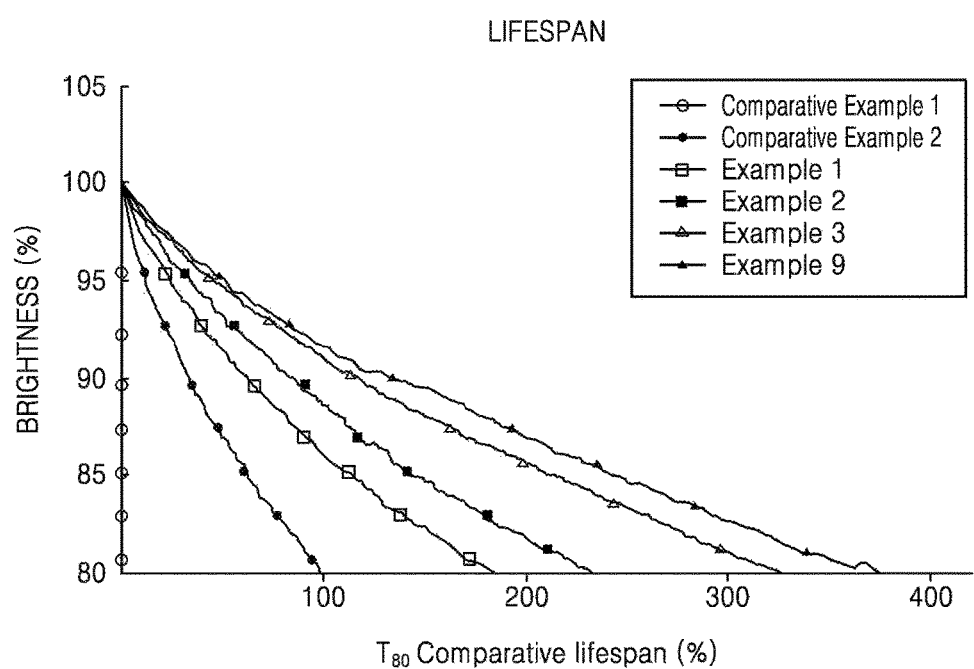
FIG. 2 shows a lifespan-luminance graph of brightness (percent, %) versus $T_{80}$ comparative lifespan (percent, %) of organic light-emitting devices manufactured according to Comparative Examples 1 and 2, and Examples 1, 2, 3 and 9.
Figure 3:
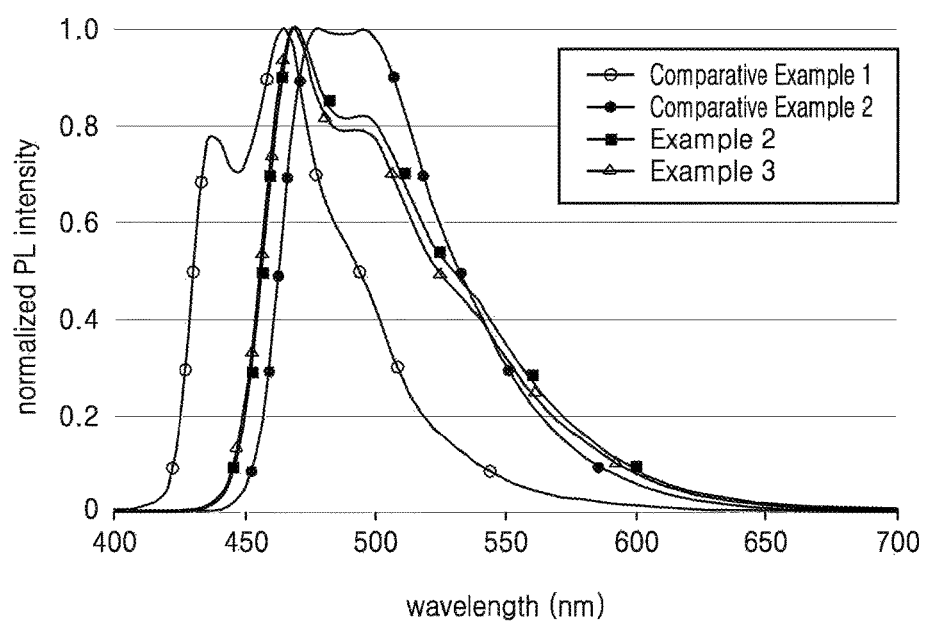
FIG. 3 is a graph of normalized photoluminescence (PL) intensity versus wavelength (nanometers, nm) showing photoluminescent (PL) spectra of organic light-emitting devices manufactured according to Comparative Examples 1 and 2, and Examples 2 and 3.

Evaluation Example 2: Evaluation of Characteristics of Organic Light-Emitting Device The organic light-emitting devices of Examples 1 to 12 and Comparative Examples 1 and 2 were evaluated in terms of changes in current density, changes in brightness, emission efficiency, and lifespan. Detailed measurement methods are described below, and results obtained therefrom are shown in Table 3 below. Lifespan data of the organic light-emitting devices of Comparative Examples 1 and 2 and Examples 1, 2, 3, and 9 is shown in FIG. 2. Electroluminescent (EL) spectra of the organic light-emitting devices of Comparative Examples 1 and 2 and Examples 2 and 3 are shown in FIG. 3.

(1) Measurement of Changes in Current Density According to Changes in Voltage

A voltage-current meter (Keithley 2400) was used with respect to the manufactured organic light-emitting device. Here, a voltage was increased from 0 Volts (V) to 10 V while a current flowing in a unit device was measured. Measurement results are obtained by dividing the measured current value by an area of the unit device.

(2) Measurement of Changes in Brightness According to Changes in Voltage

A brightness measuring meter (Minolta Cs-1000A) was used with respect to the manufactured organic light-emitting devices. Accordingly, brightness values thereof were measured when a voltage was increased from 0 V to 10 V.

(3) Measurement of Emission Efficiency

Based on the brightness values measured according to Evaluation Examples 2(1) and 2(2) and a current density and a voltage, current efficiency (candelas per Ampere, cd/A) of the manufactured organic light-emitting devices in the same current density (i.e., 10 milli Amperes per square centimeter ($mA/cm^2$)) was calculated.

(4) Measurement of Lifespan

Each organic light-emitting device was subjected to measure times taken to reduce the brightness values of Evaluation Example 2(2) to 80%. Here, a lifespan at $T_{80}$ of the organic light-emitting device of Comparative Example 2 was considered as a basis of 100, and accordingly, relative lifespan data at $T_{80}$ of the organic light-emitting devices of Examples 1 to 12 and Comparative Example 1 is shown in Table 3 below.

(5) Measurement of EL Spectrum and CIE Color Coordinate

CIE coordinates of the manufactured organic light-emitting devices were obtained from EL spectra thereof which was measured by using a brightness measuring meter (Minolta Cs-1000A) at a brightness of 500 candelas per square meter ($cd/m^2$).

TABLE 3

| | Host | Dopant | Driving voltage (V) | Current efficiency (cd/A) | Brightness ($cd/m^2$) | Comparative lifespan at $T_{80}$ (%) | Color coordinate CIEx | CIEy |
|---|---|---|---|---|---|---|---|---|
| Example 1 | mCP | BD01 | 3.8 | 34.3 | 500 | 185 | 0.19 | 0.41 |
| Example 2 | mCP | BD02 | 3.6 | 36.5 | 500 | 230 | 0.18 | 0.37 |
| Example 3 | mCP | BD03 | 3.4 | 37.6 | 500 | 325 | 0.18 | 0.36 |
| Example 4 | mCP | BD04 | 3.5 | 37.1 | 500 | 305 | 0.18 | 0.36 |
| Example 5 | mCP | BD05 | 3.5 | 35.0 | 500 | 300 | 0.17 | 0.34 |
| Example 6 | mCP | BD08 | 3.4 | 37.7 | 500 | 335 | 0.18 | 0.36 |
| Example 7 | mCP | BD07 | 3.4 | 37.9 | 500 | 340 | 0.18 | 0.36 |
| Example 8 | mCP | BD08 | 3.4 | 37.7 | 500 | 300 | 0.18 | 0.35 |
| Example 9 | mCP | BD09 | 3.5 | 38.5 | 500 | 375 | 0.19 | 0.39 |
| Example 10 | mCP | BD10 | 3.5 | 38.8 | 500 | 360 | 0.18 | 0.39 |
| Example 11 | mCP | BD11 | 3.4 | 36.8 | 500 | 300 | 0.18 | 0.36 |
| Example 12 | mCP | BD12 | 3.6 | 35.7 | 500 | 290 | 0.18 | 0.36 |
| Comparative Example 1 | mCP | A | 8.9 | 8.5 | 500 | 0.4 | 0.15 | 0.13 |
| Comparative Example 2 | mCP | B | 4.9 | 24.2 | 500 | 100 | 0.20 | 0.43 |

According to Table 3 above, it was confirmed that the organic light-emitting devices of Examples 1 to 12 exhibited significantly improved driving voltage, current efficiency, and lifespan characteristics, compared to those of the organic light-emitting device of Comparative Example 1.

According to Table 3 above, it was also confirmed that the organic light-emitting devices of Examples 1 to 12 exhibited short wavelengths, compared to the organic light-emitting device of Comparative Example 2. It was also confirmed that the organic light-emitting devices of Examples 1 to 12 exhibited significantly improved driving voltage, current efficiency, and lifespan characteristics, compared to those of the organic light-emitting device of Comparative Example 2.

An organometallic compound according to embodiments may have excellent optical characteristics, electric characteristics, and thermal stability, and accordingly, an organic light-emitting device including the organometallic compound may have a low driving voltage, high efficiency, long lifespan, and high color purity characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. An organometallic compound represented by Formula 1:

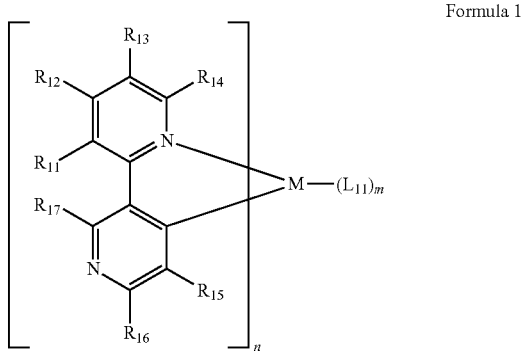

Formula 1 wherein, in Formula 1,

M is selected from a Period 4 transition metal, a Period 5 transition metal, and a Period 6 transition metal, EU, Tb, and Tm;

$R_{11}$ to $R_{17}$ are each independently selected from hydrogen, deuterium, —F, —Cl, —Br, —I, a cyano group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$); two adjacent groups selected from $R_{11}$ to $R_{16}$ are optionally linked to each other to form a saturated or unsaturated ring;

$R_{17}$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$Q_1$ to $Q_3$ are each independently selected from a substituted or unsubstituted $C_1$-$C_{60}$ alkyl group, a substituted or unsubstituted $C_3$-$C_{10}$ cycloalkyl group, a substituted or unsubstituted $C_6$-$C_{60}$ aryl group, and a substituted or unsubstituted $C_1$-$C_{60}$ heteroaryl group;

n is selected from 1, 2, and 3;

$L_{11}$ is selected from a monodentate ligand and a bidentate ligand; and m is selected from 0, 1, 2, 3, and 4.

2. The organometallic compound of claim 1, wherein M is selected from Ir, Pt, Os, Ru, Rh, Pd, Cu, Ag, Au, Ti, Zr, Hf, Eu, Tb, and Tm.

3. The organometallic compound of claim 1, wherein M is selected from Ir and Pt.

4. The organometallic compound of claim 1, wherein M is Ir.

5. The organometallic compound of claim 1, wherein $R_{11}$ to $R_{17}$ are each independently selected from hydrogen, deuterium, —F, —Cl, —Br, —I, a substituted or unsubstituted $C_1$-$C_{60}$ alkyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

two adjacent groups selected from of $R_{11}$ to $R_{16}$ are optionally linked to each other to form a saturated or unsaturated ring;

$R_{17}$ is selected from a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and $Q_1$ to $Q_3$ are each independently selected from a substituted or unsubstituted $C_1$-$C_{60}$ alkyl group and a substituted or unsubstituted $C_6$-$C_{60}$ aryl group.

6. The organometallic compound of claim 1, wherein $R_{11}$ to $R_{17}$ are each independently selected from hydrogen, deuterium, —F, —Cl, —Br, —I, a $C_1$-$C_{20}$ alkyl group, a $C_1$-$C_{20}$ alkoxy group, a $C_3$-$C_{10}$ cycloalkyl group, and a $C_1$-$C_{10}$ heterocycloalkyl group, a $C_1$-$C_{20}$ alkyl group, a $C_1$-$C_{20}$ alkoxy group, a $C_3$-$C_{10}$ cycloalkyl group, and a $C_1$-$C_{10}$ heterocycloalkyl group, each substituted with at least one selected from deuterium, —F, —Cl, —Br, and —I;

a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group;

a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from deuterium, —F, —Cl, —Br, —I, a $C_1$-$C_{20}$ alkyl group, a $C_1$-$C_{20}$ alkoxy group, a phenyl group, a naphthyl group, and —Si($Q_{11}$)($Q_{12}$)($Q_{13}$); and a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from a $C_1$-$C_{20}$ alkyl group, a phenyl group, and a naphthyl group, each substituted with at least one selected from deuterium, —F, —Cl, —Br, and —I;

two adjacent groups selected from $R_{11}$ to $R_{16}$ are optionally linked to each other to form a saturated or unsaturated ring;

$R_{17}$ is selected from a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group;

a phenyl group, a naphthyl group, a phenanthrenyl group, an anthracenyl group, a triphenylenyl group, a pyrenyl group, a chrysenyl group, a pyridinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from deuterium, —F, —Cl, —Br, —I, a $C_1$-$C_{20}$ alkyl group, a $C_1$-$C_{20}$ alkoxy group, a phenyl group, and a naphthyl group; and a phenyl group, a naphthyl group, a phenanthrenyl group, an anthracenyl group, a triphenylenyl group, a pyrenyl group, a chrysenyl group, a pyrdinyl group, a pyrazinyl group, a pyrimidinyl group, a triazinyl group, a quinolinyl group, an isoquinolinyl group, a dibenzofuranyl group, and a dibenzothiophenyl group, each substituted with at least one selected from a $C_1$-$C_{20}$ alkyl group, a phenyl group, and a naphthyl group, each substituted with at least one selected from deuterium, —F, —Cl, —Br, and —I; and $Q_{11}$ to $Q_{13}$ are each independently selected from a methyl group, an ethyl group, and a phenyl group.

7. The organometallic compound of claim 1, wherein $R_{11}$ to $R_{17}$ are each independently selected from hydrogen, deuterium, —F, a methyl group, an ethyl group, an n-propyl group, an iso-propyl group, an n-butyl group, a sec-butyl group, an iso-butyl group, a tert-butyl group, an n-pentyl group, a methoxy group, an ethoxy group, a cyclopentyl group, a cyclohexyl group, and a cycloheptyl group;

a methyl group, an ethyl group, an n-propyl group, an iso-propyl group, an n-butyl group, a sec-butyl group, an iso-butyl group, a tert-butyl group, an n-pentyl group, a methoxy group, an ethoxy group, a cyclopentyl group, a cyclohexyl group, and a cycloheptyl group, each substituted with at least one selected from deuterium and —F;

a phenyl group, a naphthyl group, and a dibenzofuranyl group;

a phenyl group, a naphthyl group, and a dibenzofuranyl group, each substituted with at least one selected from deuterium, —F, a methyl group, an ethyl group, an n-propyl group, an iso-propyl group, an n-butyl group, a sec-butyl group, an iso-butyl group, a tert-butyl group, an n-pentyl group, a phenyl group, a naphthyl group, and —Si(CH$_3$)$_3$; and a phenyl group, a naphthyl group, and a dibenzofuranyl group, each substituted with at least one selected from a methyl group, an ethyl group, an n-propyl group, an iso-propyl group, an n-butyl group, a sec-butyl group, an iso-butyl group, a tert-butyl group, an n-pentyl group, a phenyl group, and a naphthyl group, each substituted with at least one selected from deuterium and —F;

two adjacent groups selected from $R_{11}$ to $R_{16}$ are optionally linked to each other to form a saturated or unsaturated ring;

$R_{17}$ is selected from a phenyl group, a naphthyl group, and a dibenzofuranyl group;

a phenyl group, a naphthyl group, and a dibenzofuranyl group, each substituted with at least one selected from deuterium, —F, a methyl group, an ethyl group, an n-propyl group, an iso-propyl group, an n-butyl group, a sec-butyl group, an iso-butyl group, a tert-butyl group, an n-pentyl group, a phenyl group, and a naphthyl group; and a phenyl group, a naphthyl group, and a dibenzofuranyl group, each substituted with at least one selected from a methyl group, an ethyl group, an n-propyl group, an iso-propyl group, an n-butyl group, a sec-butyl group, an iso-butyl group, a tert-butyl group, an n-pentyl group, a phenyl group, and a naphthyl group, each substituted with at least one selected from deuterium and —F.

8. The organometallic compound of claim 1, wherein $R_{11}$ to $R_{17}$ are each independently selected from hydrogen, deuterium, —F, a methyl group, an ethyl group, an n-propyl group, an iso-propyl group, an iso-butyl group, a tert-butyl group, a cyclopentyl group, a cyclohexyl group, —CD$_3$, —CD$_2$H, —CDH$_2$, —CF$_3$, —CF$_2$H, —CFH$_2$, and a group represented by one of Formulae 5-1 to 5-19;

two adjacent groups selected from $R_{11}$ to $R_{16}$ are optionally linked to each other to form a saturated or unsaturated ring; and $R_{17}$ is selected from groups represented by Formulae 5-1 to 5-19:

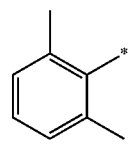

5-1

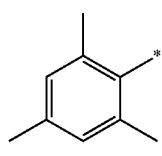

5-2

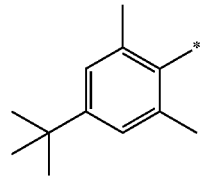

5-3

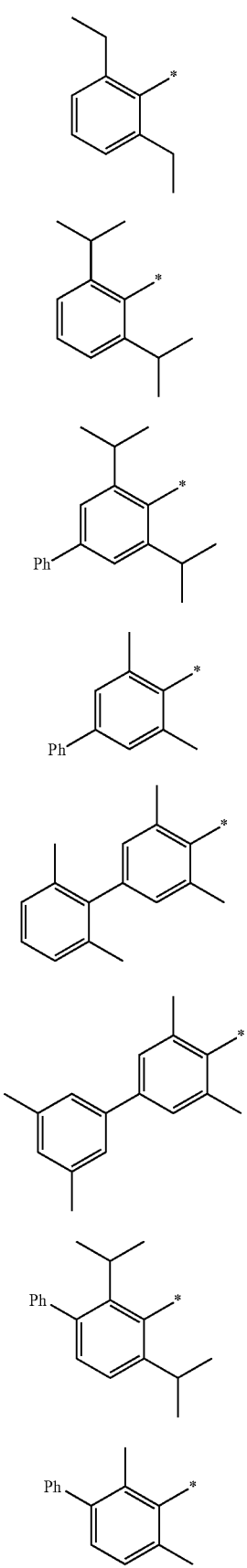
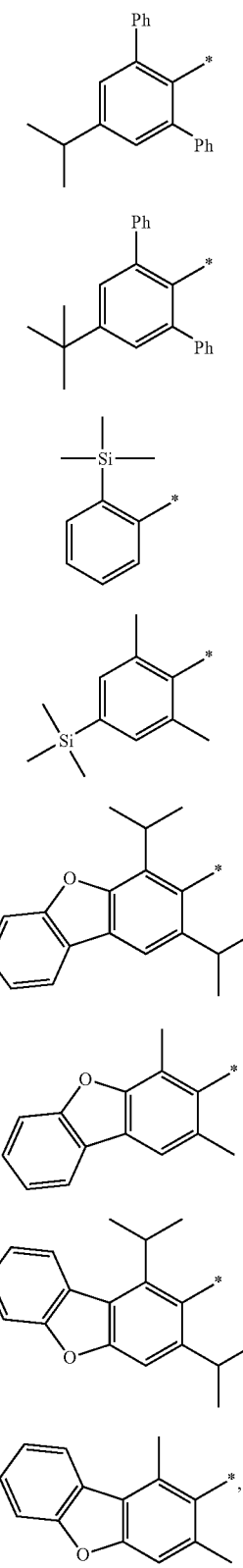
wherein, in Formulae 5-1 to 5-19,
* indicates a binding site to an adjacent atom; and
Ph indicates a phenyl group.

9. The organometallic compound of claim 1, wherein
$R_{11}$ to $R_{17}$ are each independently selected from hydrogen, deuterium, —F, a methyl group, an ethyl group, an n-propyl group, an iso-propyl group, an iso-butyl group, a tert-butyl group, a cyclopentyl group, a cyclohexyl group, —CD$_3$, —CF$_3$, and a group represented by one of Formulae 5-1 to 5-19;

two adjacent groups selected from $R_{11}$ to $R_{16}$ are optionally linked to each other to form a saturated or unsaturated ring; and $R_{17}$ is selected from groups represented by Formulae 5-1 to 5-19:

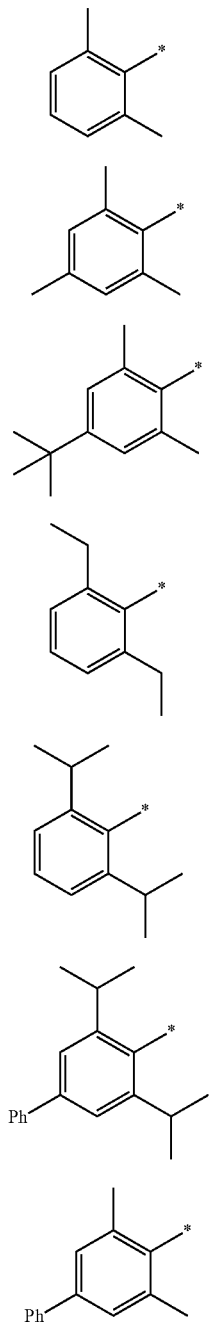

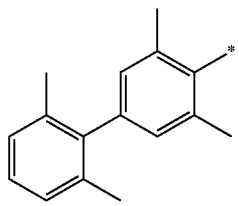

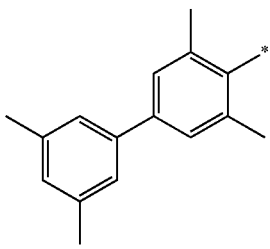

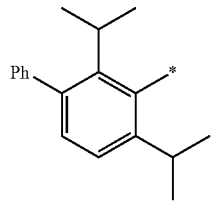

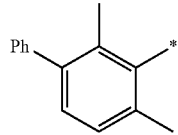

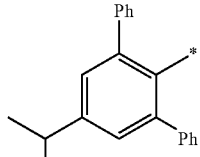

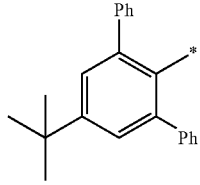

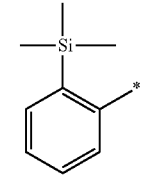

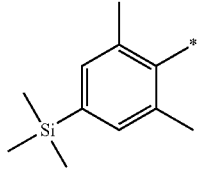

5-16

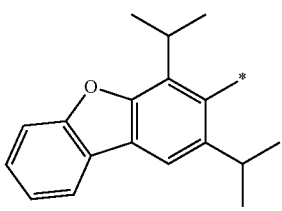

5-17

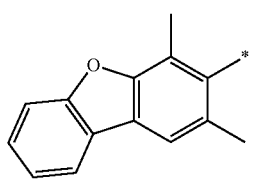

5-18

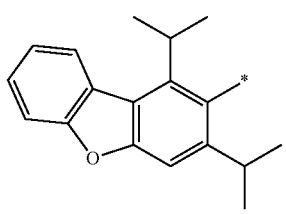

5-19

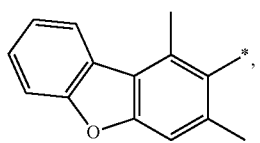

wherein, in Formulae 5-1 to 5-19,
* indicates a binding site to an adjacent atom; and
Ph indicates a phenyl group.

10. The organometallic compound of claim 1, wherein n is selected from 2 and 3.

11. The organometallic compound of claim 1, wherein $L_{11}$ is a ligand represented by one of Formulae 3-1 and 3-2:

3-1

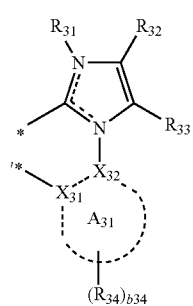

3-2

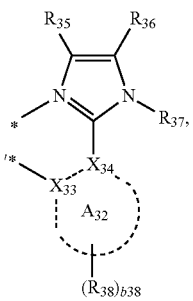

wherein, in Formulae 3-1 and 3-2, $A_{31}$ and $A_{32}$ are each independently selected from a $C_6$-$C_{20}$ carbocyclic group and a $C_1$-$C_{20}$ heterocyclic group;

$X_{31}$ to $X_{34}$ are each independently selected from C and N;

$R_{31}$ to $R_{38}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{60}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —C(=O)($Q_{31}$), —N($Q_{31}$)($Q_{32}$), and —Si($Q_{31}$)($Q_{32}$)($Q_{33}$); $R_{32}$ and $R_{33}$ are optionally linked to each other to form a saturated or unsaturated ring; $R_{35}$ and $R_{36}$ are optionally linked to each other to form a saturated or unsaturated ring;

b34 and b38 are each independently selected from 1, 2, 3, 4, 5, and 6; and

* and *' each indicate a binding site to M in Formula 1.

12. The organometallic compound of claim 1, wherein m is selected from 0 and 1.

13. The organometallic compound of claim 1, wherein the organometallic compound represented by Formula 1 is represented by groups represented by Formulae 1-1 to 1-4:

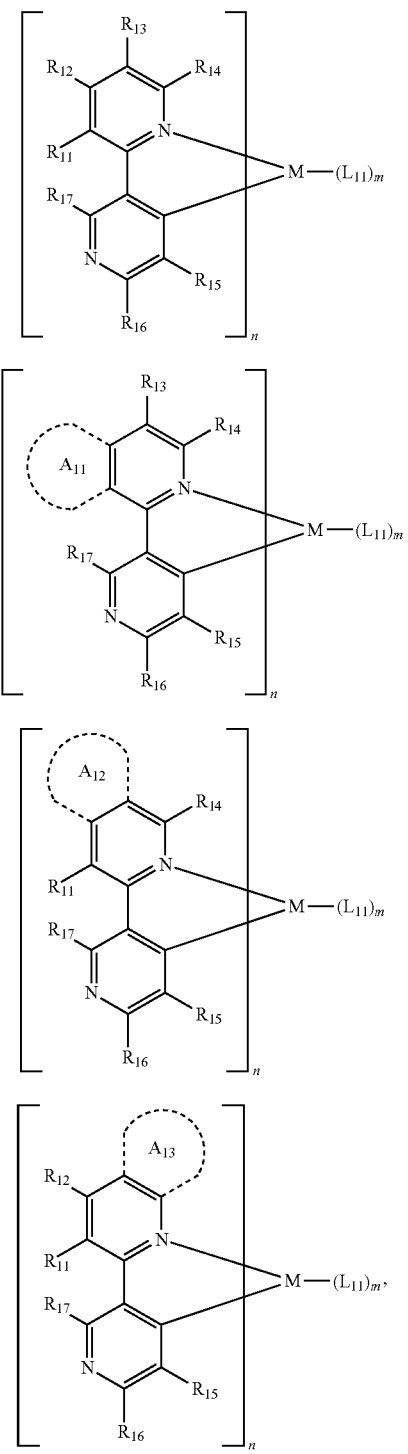

wherein, in Formulae 1-1 to 1-4, $A_{11}$ to $A_{13}$ are each independently selected from substituted or unsubstituted $C_6$-$C_{20}$ carbocyclic groups; and M, $R_{11}$ to $R_{17}$, n, $L_{11}$, and m are the same as described in connection with Formula 1.

14. The organometallic compound of claim 13, wherein $A_{11}$ to $A_{13}$ are each independently selected from a cyclopentene, a cyclohexene, and a benzene.

15. The organometallic compound of claim 1, wherein the organometallic compound represented by Formula 1 is selected from groups represented by Formulae 1-21 to 1-24:

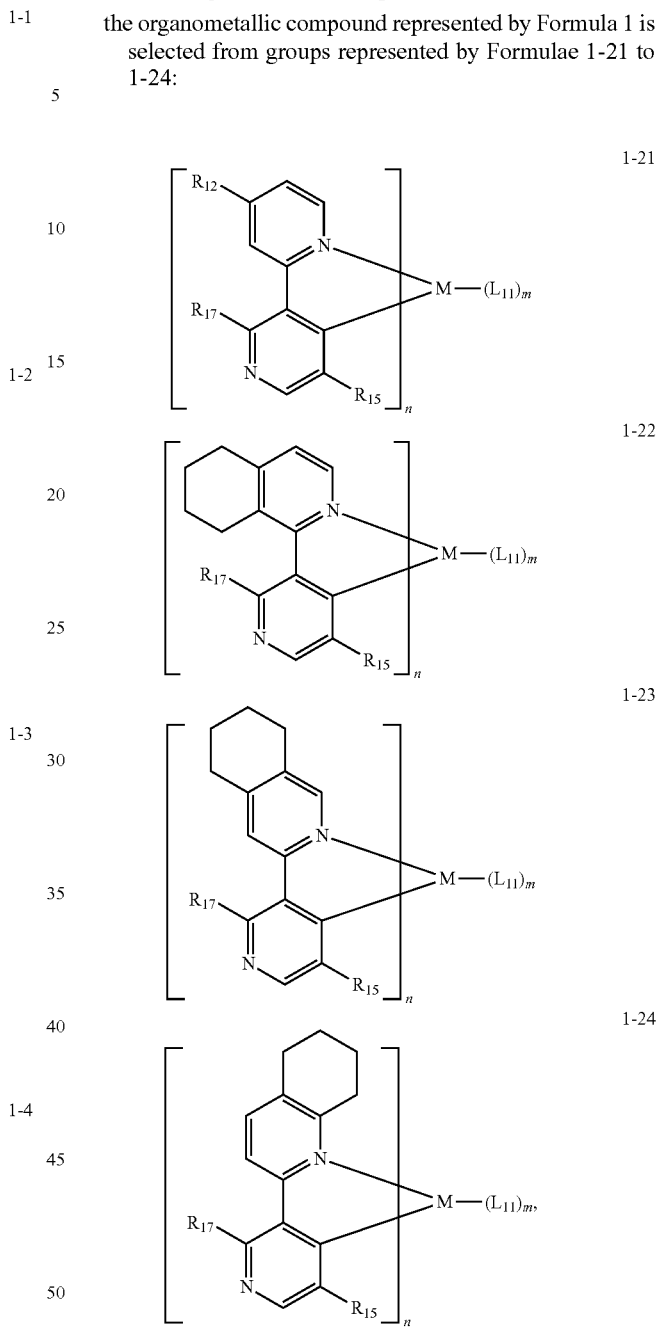

wherein, in Formulae 1-21 to 1-24,

M, $R_{12}$, $R_{15}$, $R_{17}$, n, $L_{11}$, and m are the same as described in connection with Formula 1.

16. The organometallic compound of claim 15, wherein $R_{12}$ and $R_{15}$ are each independently selected from hydrogen, deuterium, —F, a methyl group, an ethyl group, an n-propyl group, an iso-propyl group, an iso-butyl group, a tert-butyl group, a cyclopentyl group, a cyclohexyl group, —$CD_3$, —$CD_2H$, —$CDH_2$, —$CF_3$, —$CF_2H$, —$CFH_2$, and a group represented by one of Formulae 5-1 to 5-19; and $R_{17}$ is selected from groups represented by Formulae 5-1 to 5-19:

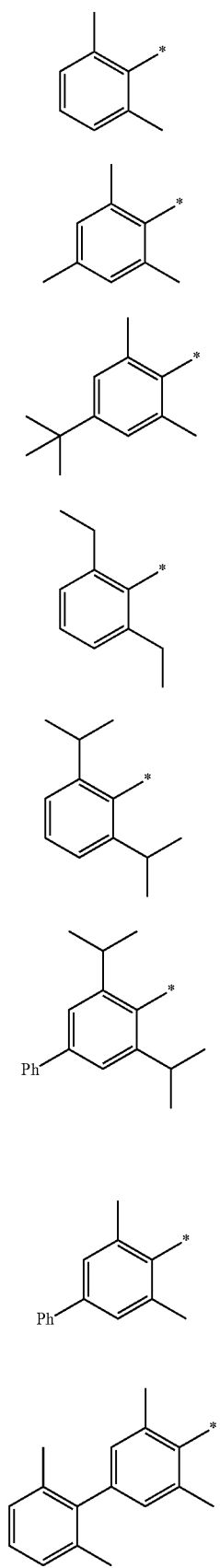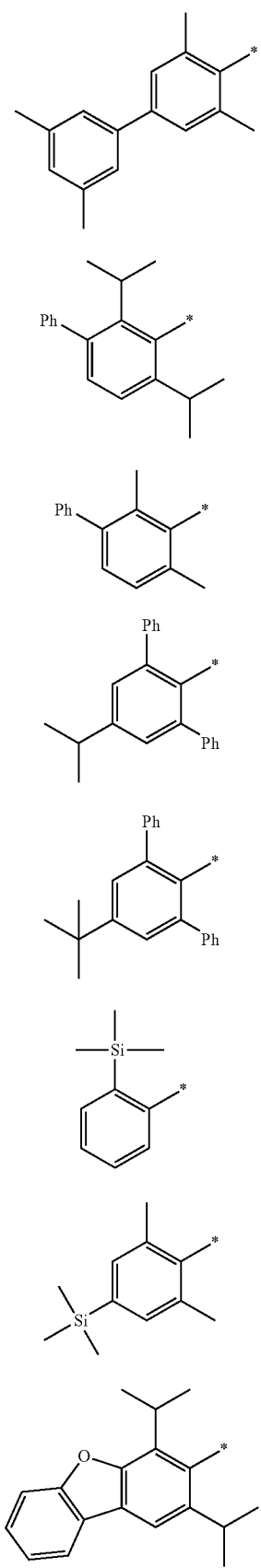

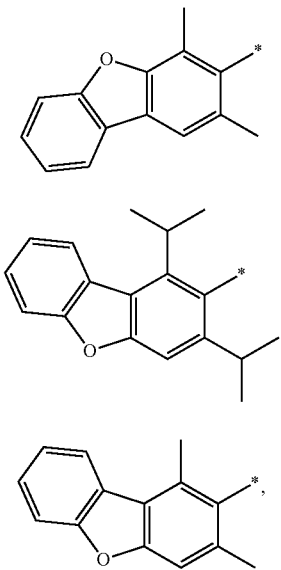
wherein, in Formulae 5-1 to 5-19,
* indicates a binding site to an adjacent atom; and
Ph indicates a phenyl group.
17. The organometallic compound of claim 1, wherein the organometallic compound represented by Formula 1 is selected from Compounds BD01 to BD12:
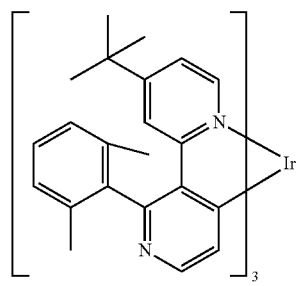
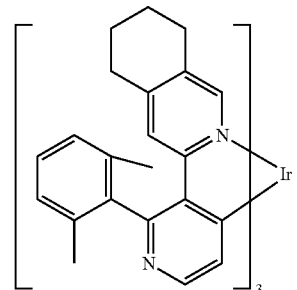
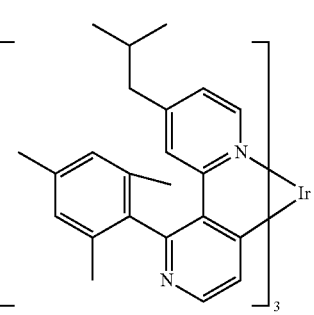
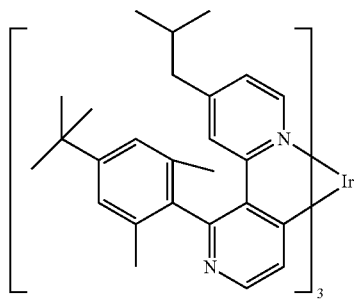
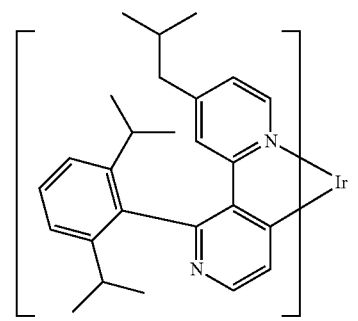

-continued

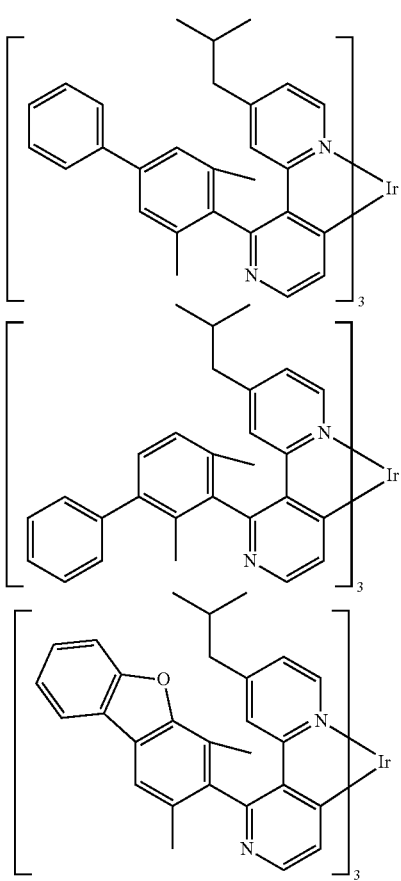

BD09

BD10

BD11

-continued

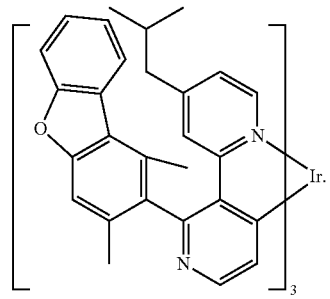

BD12

18. An organic light-emitting device comprising:
   a first electrode;
   a second electrode; and
   an organic layer disposed between the first electrode and the second electrode,
   wherein the organic layer comprises an emission layer and at least one organometallic compound of Formula 1 of claim 1.

19. The organic light-emitting device of claim 18, wherein the emission layer comprises the at least one organometallic compound of Formula 1.

\* \* \* \* \*